US008058310B2

(12) United States Patent
Dou et al.

(10) Patent No.: US 8,058,310 B2
(45) Date of Patent: Nov. 15, 2011

(54) POLYPHENOL PROTEASOME INHIBITORS, SYNTHESIS, AND METHODS OF USE

(75) Inventors: Q. Ping Dou, Grosse Pointe, MI (US); Tak-Hang Chan, Montreal (CA); David M. Smith, Boston, MA (US)

(73) Assignees: University of South Florida, Tampa, FL (US); McGill University (CA); The Hong Kong Polytechnic University, Hong Kong (HK)

( * ) Notice: Subject to any disclaimer, the term of this patent is extended or adjusted under 35 U.S.C. 154(b) by 0 days.

(21) Appl. No.: 12/660,351

(22) Filed: Feb. 25, 2010

(65) Prior Publication Data
US 2010/0173985 A1 Jul. 8, 2010

Related U.S. Application Data

(60) Division of application No. 11/820,799, filed on Jun. 20, 2007, now Pat. No. 7,767,711, which is a continuation of application No. 10/764,728, filed on Jan. 26, 2004, now Pat. No. 7,358,383.

(60) Provisional application No. 60/442,213, filed on Jan. 24, 2003, provisional application No. 60/443,554, filed on Jan. 30, 2003.

(51) Int. Cl.
*A61K 31/235* (2006.01)
*A61K 31/16* (2006.01)
(52) U.S. Cl. ........................ 514/543; 514/616
(58) Field of Classification Search .................. 514/543, 514/616
See application file for complete search history.

(56) References Cited

U.S. PATENT DOCUMENTS

| 6,713,506 B2 | 3/2004 | Dou et al. |
| 7,038,048 B2 | 5/2006 | Lu et al. |

OTHER PUBLICATIONS

Adams, J. et al. "Proteasome inhibitors: A novel class of potent and effective antitumor agents" *Cancer Res.*, 1999, 59:2615-2622.
Almond, J.B. and G.M. Cohen "The proteasome: a novel target for cancer chemotherapy" *Leukemia*, 2002, 16:433-443.
Dou, Q.P. et al. "Interruption of tumor cell cycle progression through proteasome inhibition: implications for cancer therapy" *Prog. Cell Cycle Res.*, 2003, 5:441-446.
Dou, Q.P. And B. Li "Proteasome inhibitors as potential novel anti-cancer agents" *Drug Resis. Updates*, 1999, 2:215-223.
Kazi, A. et al. "Inhibition of the proteasome activity, a novel mechanism associated with the tumor cell apoptosis-inducing ability of genistein" *Biochem. Pharm.*, 2003, 66:965-976.
Kazi, A. et al. "A natural *musaceas* plant extract inhibits proteasome activity and induces apoptosis selectively in human tumor and trans-formed, but not normal and non-transformed, cells" *Inter. J. Mol. Med.*, 2003, 12:879-887.
Kisselev, A. and A.L. Goldberg "Proteasome inhibitors: from research tools to drug candidates" *Chem. & Biol.*, 2001, 8:739-758.
Li, B. and Q.P. Dou "Bax degradation by the ubiquitin/proteasome-dependent pathway: Involvement in tumor survival and progression" *PNAS*, 2000, 97(8):3850-3855.
Nam, S. et al. "Ester bond-containing tea polyphenols potently inhibit proteasome activity in vitro and in vivo" *J. Biol. Chem.*, 276:13322-13330.
Pagano, M. et al. "Role of the ubiquitin-proteasome pathway in regulating abundance of the cyclin-dependent kinase inhibitor p27" *Science*, 1995, 269:682-685.
Verma, I.M. et al. "Rel/Nf-kB/IkB family: intimate tales of associa-tion and dissociation" *Genes & Devel.*, 1995, 9:2723-2735.
Kazi, A. et al "Inhibition of Bcl-$X_L$ phosphorylation by tea polyphenols or epigallocatechin-3-gallate is associated with prostate cancer cell apoptosis" *Mol. Pharmacology*, 2002, 62(4):765-771.
Kazi, A. et al. "Potential molecular targets of tea polyphenols in human tumor cells: significance in cancer prevention" In Vivo, 2002, 16(6):397-403.
Smith, D.M. et al. "Docking studies and model development of tea polyphenol proteasome inhibitors: Applications to rational drug design" *Proteins*, 2004, 54:58-70.
Smith, D.M. et al. "Synthetic analogs of green tea polyphenols as proteasome inhibitors" *Mol. Med.*, 2002, 8(7):382-392.
Smith, D.M. and Dou, Q.P. "Green tea polyphenol epigallocatechin inhibits DNA replication and consequently induces leukemia cell apoptosis" *Int. J. Mol. Med.*, 2001, 7(6):645-652.
Chen, C. et al. "Activation of antioxidant-response element (ARE), mitogen-activated protein kinases (MAPKs) and caspases by major green tea polyphenol components during cell survival and death" *Arch. Pharm. Res.*, 2000, 23(6):605-612.
Chung, J.Y. et al. "Mechanisms of inhibition of the Ras-MAP kinase signaling pathway in 30.7b Ras 12 cells by tea polyphenols (−)-epigallocatechin-3-gallate and theaflavin-3,3'-digallate" *FASEB J.*, 2001, 15:2022-2024.
Masuda, M. et al. "Effects of epigallocatechin-3-gallate on growth, epidermal growth factor receptor signaling pathways, gene expres-sion, and chemosensitivity in human head and neck squamous cell carcinoma cell lines" *Clin. Cancer Res.*, 2001, 7:4220-4229.
Yang, C.S. and Wang, Z-Y "Tea and Cancer" *J. Natl. Cancer Inst.*, 1993, 85(13):1038-1049.
Yu, R. et al. "Activation of mitogen-activated protein kinases by green tea polyphenols: potential signaling pathways in the regulation of antioxidant-responsive element-mediated Phase II enzyme gene expression" *Carcinogenesis*, 1997, 18(2):451-456.
Litkei, G. et al. "Flavonoids. XXV. Reaction of 2'-OR-chalcone dibromide with ammonia. Preparation of chalcone aziridine and 3-aminoflavanone" *Acta Chimica Academiae Scientiarum Hungaricae*, 1973, 76(1):95-105, abstract.
Haslam, E. et al. "Gallotannins. Part I. Introduction: and the Frac-tionation of Tannase" and "Gallotannins. Part II. Some Esters and Depsides of Gallic Acid" *J. Chem. Soc.*, 1961, 1829-1835 & 1836-1842.
Nam, S. et al. "Tannic acid potently inhibits tumor cell proteasome activity, increases p27 and Bax expression, and induces $G_1$ arrest and apoptosis" *Cancer Epidemiology, Biomarkers & Prevention*, 2001, 10:1083-1088.
Cerbai, G. et al. "Amides of substituted benzoic and cinnamic acids" *Gazzetta Chimica Italiana*, 1962, 92:420-427, abstract.

*Primary Examiner* — Janet Andres
*Assistant Examiner* — John Mabry
(74) *Attorney, Agent, or Firm* — Saliwanchik, Lloyd & Eisenschenk

(57) ABSTRACT

The present invention relates to synthetic green tea derived polyphenolic compounds, their modes of syntheses, and their use in inhibiting proteasomal activity and in treating cancers. The present invention is also directed to pharmaceutical com-positions useful in methods of inhibiting proteasomes and of treating cancers.

14 Claims, 31 Drawing Sheets
(8 of 31 Drawing Sheet(s) Filed in Color)

FIG. 3A  FIG. 3B

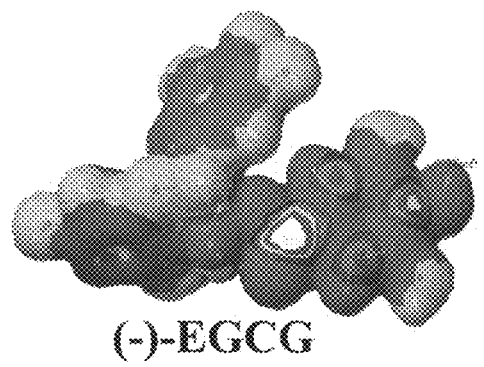
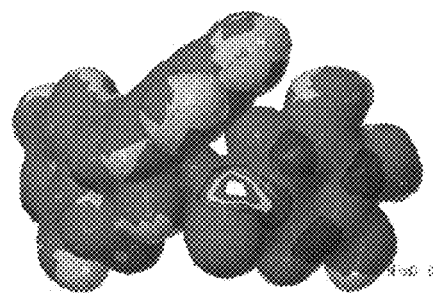
(-)-EGCG          (-)-EGCG-Amide
FIG. 4A          FIG. 4B
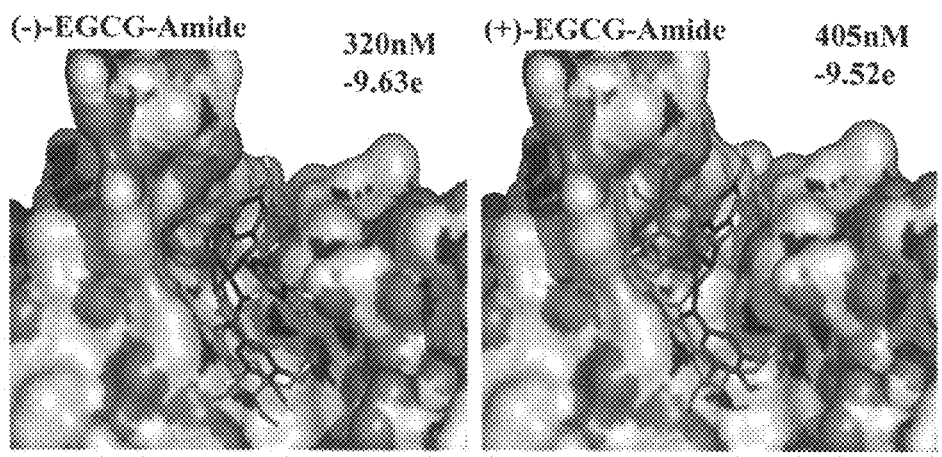
FIG. 4C          FIG. 4D

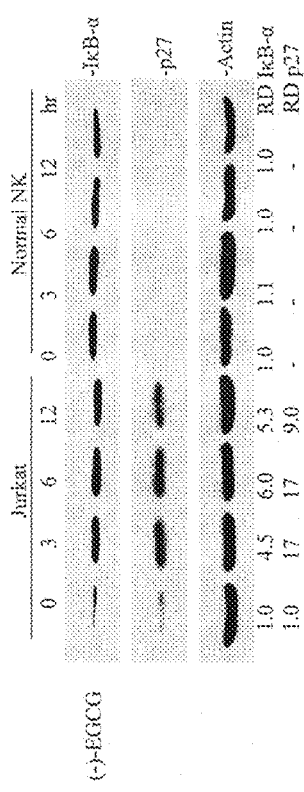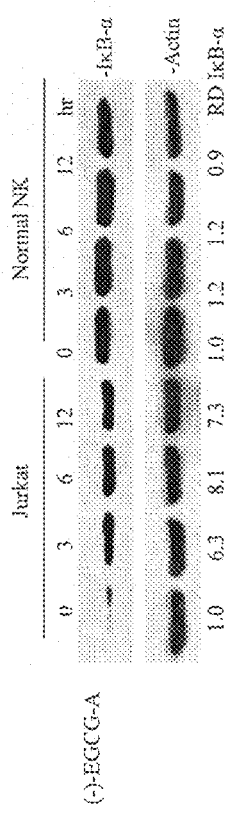
FIG. 13A
FIG. 13B

One aspect of
POLYPHENOL PROTEASOME INHIBITORS, SYNTHESIS, AND METHODS OF USE

CROSS-REFERENCE TO RELATED APPLICATIONS

The present application is a divisional of U.S. application Ser. No. 11/820,799, filed Jun. 20, 2007, which is a continuation of U.S. application Ser. No. 10/764,728, filed Jan. 26, 2004, now U.S. Pat. No. 7,358,383, which claims benefit of U.S. Provisional Application Ser. No. 60/442,213, filed Jan. 24, 2003, and U.S. Provisional Application Ser. No. 60/443,554, filed Jan. 30, 2003, which are hereby incorporated by reference herein in their entirety, including any figures, tables, nucleic acid sequences, amino acid sequences, or drawings.

BACKGROUND OF INVENTION

The proteasome is a massive multi-catalytic protease complex that is responsible for degrading the majority of cellular proteins. The 20S-core particle of the 26S proteasome is barrel-shaped, and the sites of proteolytic activity reside on the interior.

The eukaryotic proteasome contains three known activities that are associated with its β subunits. These are the chymotrypsin-like (cleavage after hydrophobic residues, β5 subunit), trypsin-like (cleavage after basic residues, β2 subunit), and caspase-like (cleavage after acidic residues, β1 subunit) activities.

These three activities depend on the presence of an N-terminal Thr (Thr 1) residue. The hydroxyl group on the side chain of Thr 1 is responsible for catalyzing cleavage of peptides through nucleophilic attack (addition-elimination mechanism). Near this N-terminal threonine, binding pockets recognize the side chains of peptides and give each catalytic site its specificity. The S1 pocket of the β5 subunit is defined by the hydrophobic residues, Ala 20, Val 31, Ile 35, Met 45, Ala 49, and Glu 53, and this binding pocket has been shown to be important for substrate specificity and binding of several types of proteasome inhibitors.

The ubiquitin/proteasome-dependent degradation pathway plays an essential role in upregulation of cell proliferation, down-regulation of cell death, and development of drug resistance in human tumor cells, suggesting the use of proteasome inhibitors as potential novel anticancer drugs, which has been demonstrated in various cell cultures, animal models and clinical trials. In a broad range of cell culture models, proteasome inhibitors rapidly induce tumor cell apoptosis, selectively trigger programmed cell death in the oncogene-transformed, but not normal or untransformed cells, and are able to activate the death program in human cancer cells that are resistant to various anticancer agents. Inhibition of the chymotrypsin-like, but not trypsin-like, activity has been found to be associated with induction of tumor cell apoptosis.

The proteasome degrades a number of proteins that are involved in tumor suppression. Cyclin-dependent kinase inhibitor p27, a key regulatory molecule in cell cycle progression, is one example (Pagano, M. et al. *Science*, 1995, 269:682-685). Inhibition of the proteasome results in an accumulation of ubiquitinated and unmodified p27' that can result in $G_1$ cell cycle arrest (An, B. et al. *Cell Death Differ,* 1998, 5:1062-75; Sun, J. et al. *Cancer Res,* 2001, 61:1280-1284). Additionally, inhibition of the proteasome increases the intracellular concentrations of IκB-a (Palombella, V. J. et al. *Cell,* 1994, 78:773-785), an inhibitor of nuclear factor kappa B (NFκB), leading to inhibition of NFκB activation (Thompson, J. E. et al. *Cell,* 1995, 80:573-582) and reduction of anti-apoptotic gene signaling (Perkins, N. D. *Trends Biochem Sci,* 2000, 25:434-440). Another effect of proteasome inhibition is the accumulation of mitochondrial proapoptotic protein Bax, a Bcl-2 family member (Chang, Y. C. et al. *Cell Growth Differ,* 1998, 9:79-84; Li, B. and Dou, Q. P. *Proc Natl Acad Sci USA,* 2000, 97:3850-3855; Nam, S. et al. *Cancer Epidemiol Biomarkers Prev,* 2001, 10:1083-1088), resulting in the release of cytochrome c from the mitochondria and activation of caspase-mediated apoptosis (Green, D. R. and Reed, J. C. *Science,* 1998, 281:1309-1312).

In different animal studies, proteasome inhibitors suppress tumor growth via induction of apoptosis and inhibition of angiogenesis. MLN-341 (formerly PS-341) is a potent and selective dipeptidyl boronic acid compound, which inhibits the chymotrypsin-like activity of the 20S proteasome. This proteasome inhibitor is currently being developed for the potential treatment of human hematological malignant neoplasms and solid tumors. Preliminary data from Phase I and II clinical trials confirm the anti-tumor activity of MLN-341 although some associated side effects were observed. The proteasome inhibition mechanism of MLN-341 has not been confirmed by X-ray diffraction experiments.

However, the proteasome-inhibition mechanism of another peptide inhibitor, LLnL, and nonpeptide inhibitors, such as lactacystin and the macrocyclic compound TMC-95, have been confirmed by X-ray diffraction. Understanding how these inhibitors function at the molecular level will give insight into the structural studies of other proteasome inhibitors where X-ray crystal structures are not available. These studies thereby demonstrate that the proteasome is an excellent target for developing pharmacological anti-cancer drugs.

Tea, the most popular beverage in the world, is consumed by over two-thirds of the world's population. Several epidemiological studies have provided evidence for the cancer-preventive properties of green tea. Furthermore, animal studies have also suggested that green tea polyphenols could suppress the formation and growth of various tumors. Although numerous cancer-related proteins are affected by tea polyphenols, the molecular basis for tea-mediated cancer prevention remains unknown.

The naturally occurring ester bond-containing green tea polyphenols (GTPs), such as (−)-epigallocatechin-3-gallate (also referred to herein as (−)-EGCG, and shown in FIG. 1), possess the ability to inhibit proteasome activity both in vitro and in vivo. Recently completed Phase I clinical trials using (−)-EGCG and green tea to treat cancer and prevent reoccurrence indicate a wide tolerance to green tea (up to 7-8 cups/per day) (Pisters, K. M. et al. *J Clin Oncol,* 2001, 19:1830-1838). The lack of toxicity to normal cells observed in clinical trials and effectiveness of treatment confirm the results from the cell culture models (Adams, J. et al. *Cancer Res,* 1999, 59:2615-2622; Dou, Q. P. and Li, B. et al. *Drug Resist Updat,* 1999, 2:215-223; Almond, J. B. and Cohen, G. M. Leukemia, 2002, 16:433-443; Kisselev, A. F. and Goldberg, A. L. *Chem Biol,* 2001, 8:739-758). In addition, synthetic GTPs with an ester bond, such as (+)-EGCG (shown in FIG. 1), are also able to potently and selectively inhibit the chymotrypsin-like activity of the proteasome. It appears that a center of nucleophilic susceptibility resides at the ester bond carbon in these polyphenols. This proposed mechanism of ester bond-based nucleophilic attack is similar to that of lactacystin-based inhibition. However, a need still exists for more options in inhibiting proteasome activity.

BRIEF SUMMARY OF THE INVENTION

Synthetic green tea polyphenol compounds potently inhibit proteasomal chymotrypsin-like activity. One aspect of the present invention pertains to synthetic green tea-derived polyphenolic compounds useful for inhibiting proteasomal chymotrypsin-like activity. Polyphenolic compounds of the present invention include (−)-EGCG-amides, (+)-EGCG-amides, and pharmaceutically acceptably salts and analogs of these compounds. Other polyphenolic compounds of the present invention include those represented by the structures (formulas) shown in FIG. 8.

Another aspect of the present invention provides methods of synthesizing (−)-EGCG-amides and (+)-EGCG-amides. Advantageously, the reagents and steps of the method of the invention can be easily adjusted to produce stereoisomers of the products, if desired.

Another aspect of the present invention is directed to methods of using the polyphenolic compounds of the invention. In one embodiment, a method to inhibit proteasomal activity is disclosed. Advantageously, proteasomal inhibition can take place in vivo or in vitro. In yet another embodiment, a method for treating cancers is provided.

Another aspect of the present invention provides for pharmaceutical compositions containing polyphenolic compounds of the invention and pharmaceutically acceptable carriers or diluents.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 3A shows the binding mode of (−)-EGCG.
FIG. 3B-1 shows an overlap of (−)-EGCG and (+)-EGCG (green) binding modes.

FIG. 4A shows the nucleophilic susceptibility of (−)-EGCG. The white center signifies the highest area of nucleophilic susceptibility.

FIG. 4B shows the nucleophilic susceptibility of (−)-EGCG-Amide. The white center signifies the highest area of nucleophilic susceptibility.

FIG. 4C shows the binding mode of (−)-EGCG-Amide.
FIG. 4D shows the binding mode of (+)-EGCG-Amide.

FIG. 13A shows the selective accumulation of p27 and IκB-a proteins in leukemic Jurkat T over non-transformed NK cells when treated by (−)-EGCG.

FIG. 13B shows the selective accumulation of p27 and IκB-a proteins in leukemic Jurkat T over non-transformed NK cells when treated by (−)-EGCG-amide.

DETAILED DISCLOSURE OF THE INVENTION

The present invention is directed to polyphenolic compounds useful for inhibiting proteasomal activity, methods of synthesis and use in proteasome inhibition and treating cancer, and pharmaceutical compositions. In particular, the polyphenolic compounds of the present invention inhibit the chymotrypsin-like activity of a proteasome's $\beta_5$ subunit. The polyphenolic compounds of the present invention may be synthesized using methods disclosed herein.

One embodiment of the subject invention is directed to polyphenolic compounds having a similar ring structure to green tea polyphenols. More particularly, the compounds of the present invention possess an adequate number of substituents to the phenols or carbonyl oxygens to ensure favorable binding of the compounds to the $\beta_5$ subunit's active site. Subsequently, these compounds are capable of attack by the N-terminal Threonine (Thr 1) via acylation.

Advantageously, the compounds of the present invention are an irreversible mechanism-based inhibitor of the chymotrypsin-like activity of 20S proteasome.

Figure 1:
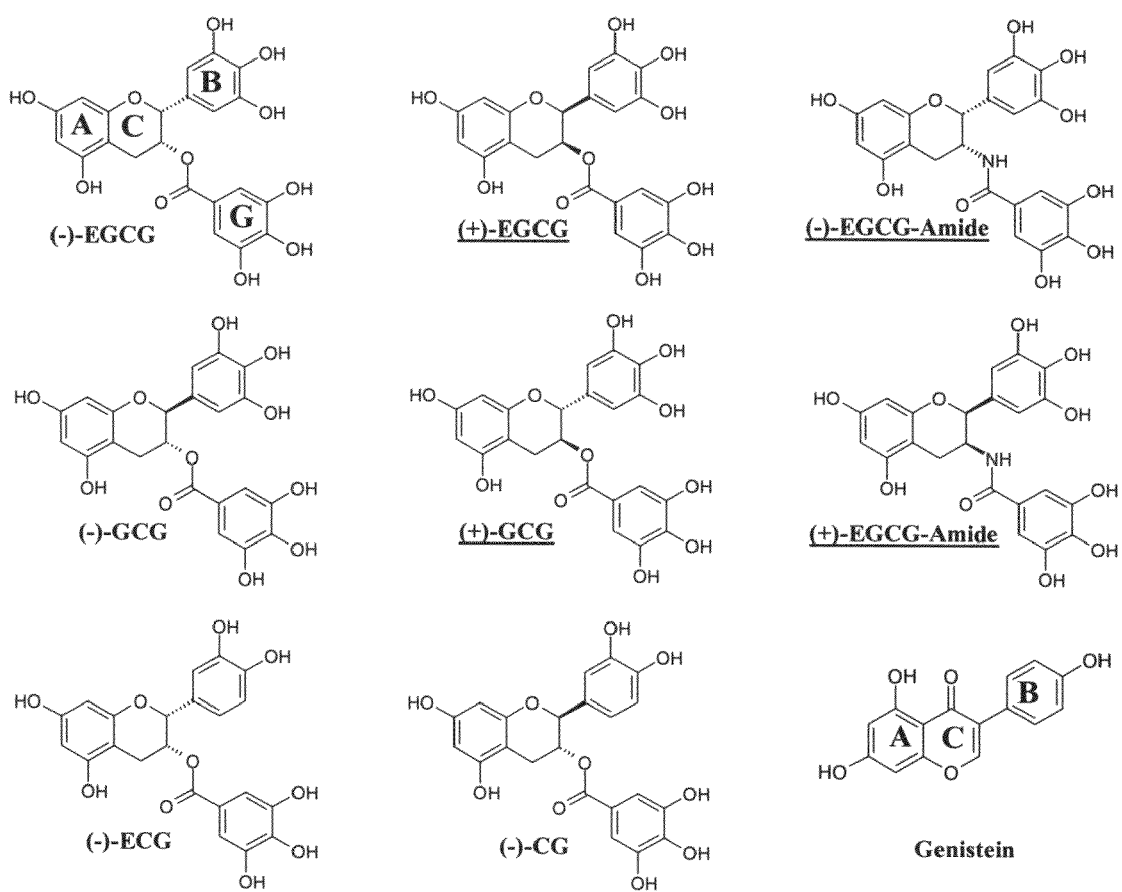
FIG. 1 shows structures of green tea polyphenols (GTPs) and synthetic (−)-EGCG and (+)-EGCG amides.

The nomenclature of FIG. 1, whereby the rings of (−)-EGCG are named A, B, C or G, is utilized throughout the text.

In accordance with another embodiment of the present invention, there is provided a compound having structure I:

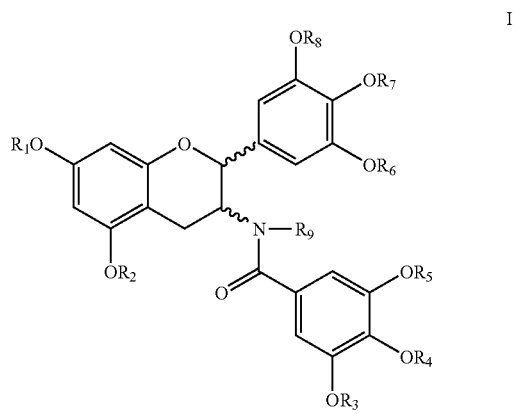

wherein $R_1$-$R_8$ are independently selected from the group consisting of H, alkyl, alkenyl, cycloalkyl, heterocycloalkyl, cycloalkenyl, heterocycloalkenyl, aryl, and acyl group, any of which may be optionally substituted; and $R_9$ is selected from the group consisting of H, alkyl group, alkenyl, cycloalkyl, heterocycloalkyl, cylcoalkenyl, heterocycloalkenyl, acyl, and aryl, any of which may be optionally substituted.

Optionally, formula I can be drawn as four separate two-dimensional Fisher Projection Formulations to represent the B ring of I projecting out and behind the A and C rings and the G ring of I projecting out and behind the A and C rings.

In a specific embodiment, $R_1$-$R_8$ is selected from the group consisting of —H, alkyl, and acyl, and $R_9$ is selected from the group consisting of —H, alkyl, and aryl.

In a preferred embodiment, the carbonyl of both (+)-EGCG-amide and (−)-EGCG-amide compounds is susceptible to a nucleophilic attack due to the presence of the amide nitrogen. As shown in FIGS. 4A and 4B, molecular orbital calculations confirmed that the amide bond-carbon produced an arbitrary value of 0.55 for nucleophilic susceptibility. In contrast, the same carbon in (−)-EGCG has a value of 0.69.

Introduction of a nitrogen atom into EGCG, as in EGCG-amide, reduces bond flexibility. It is known that such an amide bond (or peptide bond) is less flexible than the ester bond and prefers the trans conformation.

Figure 4E:
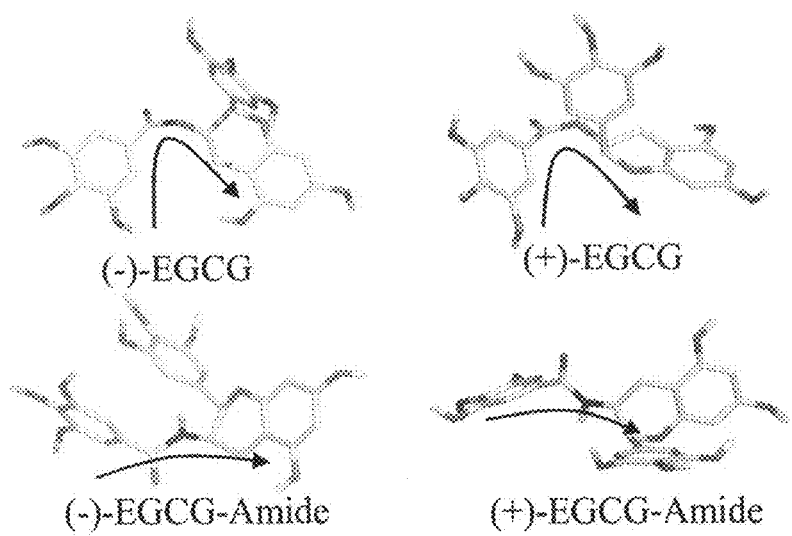
FIG. 4E shows the bound conformation of (−)-EGCG, (+)-EGCG, (−)-EGCG-amide and (+)-EGCG-amide.

Therefore, due to the decreased flexibility of the amide bond, the amide polyphenols cannot adopt a saddle-shaped conformation that is energetically favorable for binding. This causes a straightening out of the arch conformation (FIG. 4E), which does not allow the A-C rings to bind as deeply in the S1 pocket as compared to (−)-EGCG, thus pulling the compound further out of the binding cleft. This consequently raises the binding free energy of both (−)-EGCG-amide and (+)-EGCG-amide (−9.63 and −9.52 kcal/mol, respectively; FIGS. 4C and 4D). This binding mode with increased binding free energy agrees with the increase in the $IC_{50}$ values of both amide compounds (FIG. 4) and may (along with their reduced nucleophilic susceptibility) explain their decreased potency relative to the corresponding esters.

However, the amide analogs were still able to accumulate levels of the proteasome target protein p27 in breast cancer MCF-7 cells, with potency comparable to that of (−)-EGCG.

Another aspect of the present invention provides a method for the preparation of a compound of the present invention, comprising the step of coupling a compound of formula II with an acid of formula III to form a fully protected gallate ester, wherein $R_1$-$R_9$ are independently —H, alkyl, alkenyl, cycloalkyl, heterocylcoalkyl, cycloalkenyl, heterocycloalkenyl, acyl, or aryl.

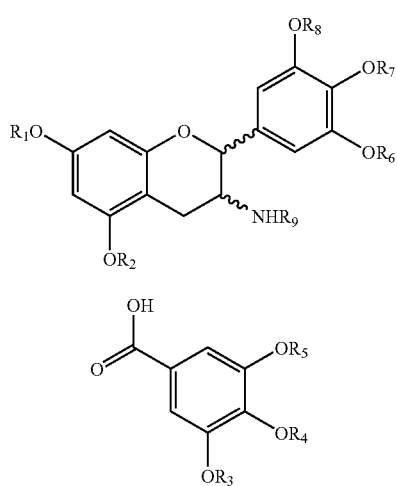

In a specific embodiment, $R_1$-$R_8$ are independently aryl, and $R_9$ is —H.

Preferably the acid of formula III is employed in the form of a derivative which is an acyl halide or a mixed or symmetric acid anhydride, more preferably the derivative is an acyl halide, or the acid of formula III is reacted with the compound of formula II in the presence of a condensing reagent.

In a preferred method of the present invention, the acid of formula III is reacted with a compound of formula II in the presence of a condensing agent, wherein said condensing agent is selected from the group consisting of 1,3-diisopropylcarbodiimide (DIPC), 1, (3-dimethylaminopropyl(3-ethyl carbodiimide (EDC), dialkyl carbodiimide, 2-halo-1-alkyl-pyridinium halides, propane phosphonic acid cyclic anhydride (PPACA), N-ethoxycarbonyl-2-ethoxy-1,2-dihydroquinoline (EEDQ) and dicyclohexylcarbodiimide (DCC).

Figure 8:
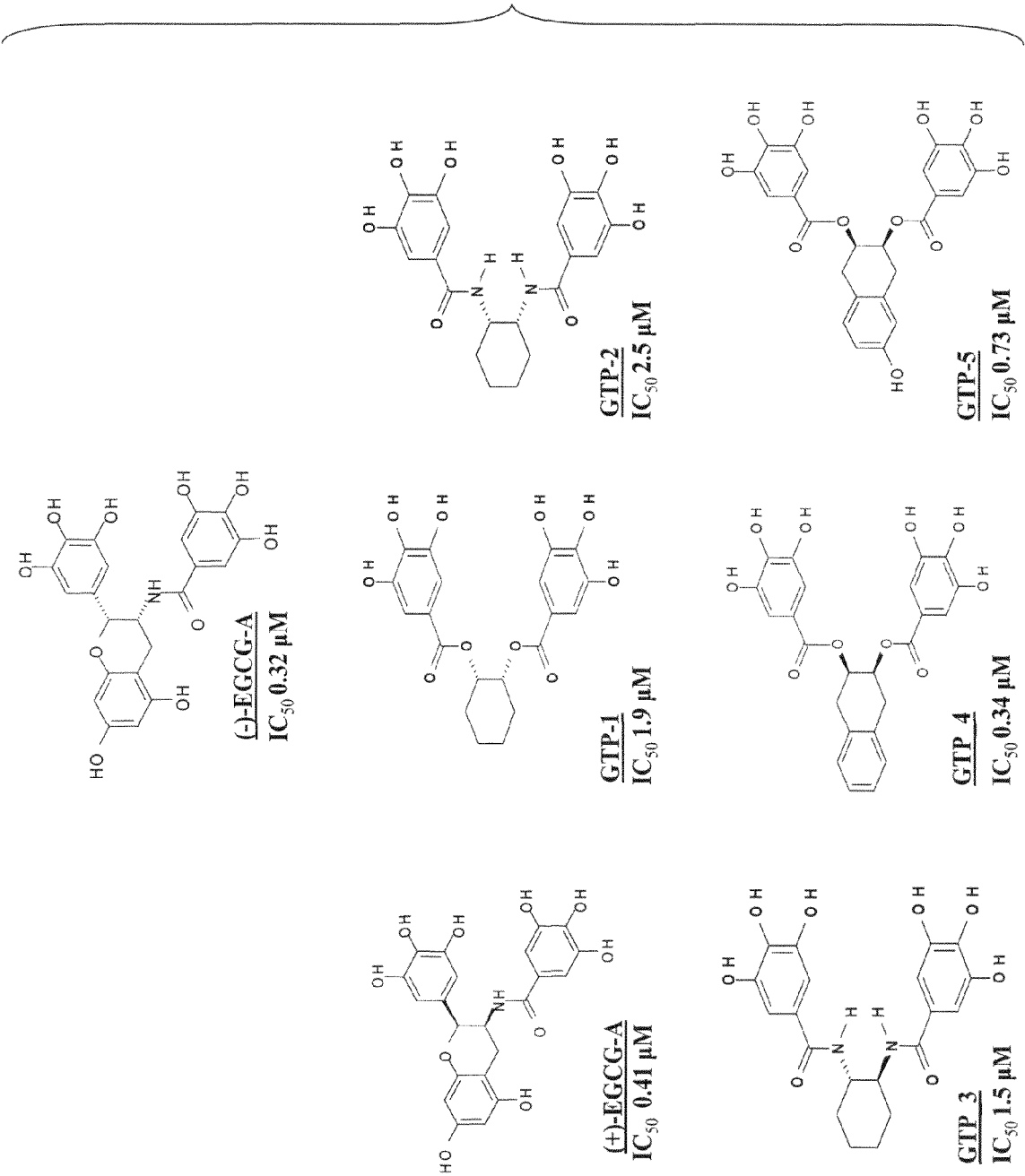
FIG. 8 shows structures of the natural tea polyphenol (−)-EGCG and eight synthetic analogs, (−)-ECGC-A, (+)-EGCG, (+)-EGCG-A, GTP-1, GTP-2, GTP-3, GTP-4 and GTP-5 and their one-half maximal inhibition values (IC50s) of 20S proteasomal activity.

Another embodiment of the present invention pertains to polyphenolic compounds having double amide and ester bonds, such as compounds having the structures of FIG. 8 and labeled GTP-1, GTP-2, GTP-3, GTP-4 and GTP-5.

Although the compounds of the present invention can be administered alone, one embodiment of the present invention is a pharmaceutical formulation comprising at least one additional active ingredient, together with one or more pharmaceutically acceptable carriers therefore. Each carrier must be acceptable in the sense of being compatible with the other ingredients of the formulation and not injurious to the patient.

Pharmaceutical compositions are useful for inhibiting chymotrypsin-like activity of 20S proteasome, 26S proteasome, treating various cancers, for inhibiting cancer cell growth, for increasing the proportion of $G_1$ cells in a population of cells (i.e., those cells occupying the $G_1$ phase of the mitotic cell cycle), and for inducing apoptosis of cells. One such composition comprises a compound selected from the group consisting of an enantiomer of an ester bond-containing tea polyphenol, an amide analog of an ester bond-containing tea polyphenol, and an amide analog of an enantiomer of an ester bond-containing tea polyphenol, in association with a pharmaceutically acceptable carrier.

In a preferred composition according to an embodiment of the present invention, the compound has less than 100% optical purity.

In a preferred composition, the tea polyphenol is selected from the group consisting of the compounds of the present invention, more preferably (+)-EGCG-amide, (−)-EGCG-amide, any of the compounds whose structures are listed in FIG. 8, pharmaceutically acceptable salts, analogs, and mixtures thereof.

Another preferred composition utilizes polyphenols having the structures of GTP-1, GTP-2, GTP-3, GTP-4 and GTP-5 (FIG. 8), pharmaceutically acceptable salts, analogs, and mixtures thereof.

Formulations include those suitable for oral, rectal, nasal, topical (including transdermal, buccal and sublingual), vaginal, parental (including subcutaneous, intramuscular, intravenous and intradermal) and pulmonary administration. The formulations can conveniently be presented in unit dosage form and can be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product. Formulations of the present invention suitable for oral administration can be presented as discrete units such as capsules, cachets or tablets, each containing a predetermined amount of the active ingredient; or as an oil-in-water liquid emulsion, water-in-oil liquid emulsion or as a supplement within an aqueous solution, for example, a tea. The active ingredient can also be presented as bolus, electuary, or paste.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents.

Formulations suitable for topical administration to the eye also include eye drops wherein the active ingredient is dissolved or suspended in a suitable carrier, especially an aqueous solvent for the agent.

Formulations for rectal administration can be presented as a suppository with a suitable base comprising, for example, cocoa butter or a salicylate.

Formulation suitable for vaginal administration can be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration by nebulizer, include aqueous or oily solutions of the agent.

Formulations suitable for parenteral administration include aqueous and non-aqueous isotonic sterile injection solutions which can contain antioxidants, buffers, bacteriostats and solutes which render the formulation isotonic with the blood of the intended recipient; and aqueous and non-aqueous sterile suspensions which can include suspending agents and thickening agents, and liposomes or other microparticulate systems which are designed to target the compound to blood components or one or more organs. The formulations can be presented in unit-dose or multi-does or multi-dose sealed containers, such as for example, ampoules and vials, and can be stored in a freeze-dried (lyophilized) condition requiring only the addition of the sterile liquid carrier, for example water for injections, immediately prior to use. Extemporaneous injection solutions and suspensions can be prepared from sterile powders, granules and tablets of the kind previously described.

Preferred unit dosage formulations are those containing a daily dose or unit, daily subdose, as herein above-recited, or an appropriate fraction thereof, of an agent. It should be understood that in addition to the ingredients particularly mentioned above, the formulations of this invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Various delivery systems are known and can be used to administer a therapeutic agent of the invention, e.g., encapsulation in liposomes, microparticles, microcapsules, receptor-mediated endocytosis and the like. Methods of delivery include, but are not limited to, intra-arterial, intramuscular, intravenous, intranasal, and oral routes. In a specific embodiment, the pharmaceutical compositions of the invention can be administered locally to the area in need of treatment; such local administration can be achieved, for example, by local infusion during surgery, by injection, or by means of a catheter.

Therapeutic amounts can be empirically determined and will vary with the pathology being treated, the subject being treated, and the efficacy and toxicity of the agent. Similarly, suitable dosage formulations and methods of administering the agents can be readily determined by those of skill in the art.

The pharmaceutical compositions can be administered by any of a variety of routes, such as orally, intranasally, parenterally or by inhalation therapy, and can take form of tablets, lozenges, granules, capsules, pills, ampoule, suppositories or aerosol form. They can also take the form of suspensions, solutions, and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

Ideally, the agent should be administered to achieve peak concentrations of the active compound at sites of the disease. Peak concentrations at disease sites can be achieved, for example, by intravenously injecting of the agent, optionally in saline, or orally administering, example, a tablet, capsule or syrup containing the active ingredient.

Advantageously, the compositions can be administered simultaneously or sequentially with other drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids.

Another aspect of the present invention is directed to methods of inhibiting proteasomal activity. In particular, the chymotrypsin activity and chymotrypsin-like activity of the 20S proteasome is inhibited.

One method of inhibiting comprises contacting a proteasomal cell with a sufficient amount of the compounds of the present invention. Advantageously, inhibition can take place in vivo or in vitro.

Another embodiment of the present invention provides a method of inhibiting chymotrypsin-like activity of 20S proteasome, comprising administering to an individual a pharmaceutically effective amount of a pharmaceutical composition of the present invention.

Preferably, the administering is carried out orally, parenterally, subcutaneously, intravenously, intramuscularly, intraperitoneally, intraarterially, transdermally or via a mucus membrane.

In accordance with another embodiment of the present invention, there is provided a method of treating cancer, comprising administering to an individual a pharmaceutically effective amount of a pharmaceutical composition of the present invention.

Preferably, a cancer to be treated in accordance with an embodiment of the present invention is selected from the group consisting of prostate cancer, leukemia, hormone dependent cancers, breast cancer, colon cancer, lung cancer, epidermal cancer, liver cancer, esophageal cancer, stomach cancer, cancer of the brain, and cancer of the kidney.

In a preferred method, the treatment is effected by inducing apoptosis of cells of the cancer.

Another embodiment of the present invention provides a method of inhibiting cancer cell growth, comprising administering to a patient a pharmaceutically effective amount of a pharmaceutical composition of the present invention.

In accordance with another embodiment of the present invention, there is provided a method of increasing relative proportion of $G_1$ cells in a population of cells, such as cancer cells, comprising administering to a patient a pharmaceutically effective amount of a pharmaceutical composition according to an embodiment of the present invention.

In accordance with another embodiment of the present invention, there is provided a method of inducing apoptosis in a population of cells, preferably cancer cells, such as LNCaP cells, by administering to the population of cells an effective amount of a composition according to an embodiment of the present invention.

For the purpose of the present invention. the following terms are defined below.

The term "inhibition" is intended to mean a substantially slowing, interference, suppression, prevention, delay and/or arrest of a chemical action.

The term "pharmacological inhibition" is intended to mean a substantially slowing, interference, suppression, prevention, delay and/or arrest of a chemical action which is caused by an effective amount of a compound, drug, or agent.

The term "inhibitor" is intended to mean a compound, drug, or agent that substantially slows, interferes, suppresses, prevents, delays and/or arrests a chemical action.

The term "green tea" is intended to mean non-fermented leaves of the tea plant *Camellia sinensis*

The term "black tea" is intended to mean fermented leaves of the tea plant *Camellia sinensis*.

The term "polyphenol" is intended to mean a compound with more than one phenolic moiety. A phenolic compound is an aromatic compound containing an aromatic nucleus to which is directly bonded at least one hydroxyl group. The term polyphenol includes, without limitation, (−)EGCG, (−)EGC, (−)ECG, and (−)EC, such as those that can be extracted from leaves of the tea plant *Camellia sinensis*, and analogs thereof, as well as structurally similar synthetic analogs.

The term "tea polyphenol" is intended to mean a polyphenol capable of being extracted/isolated from leaves of the tea plant *Camellia sinensis*, but which may be chemically synthesized. The term green tea polyphenol specifically means a polyphenol capable of being extracted from green tea leaves.

The term "alkyl group" is intended to mean a group of atoms derived from an alkane by the removal of one hydrogen atom. Thus, the term includes straight or branched chain alkyl moieties including, for example, methyl, ethyl, propyl, isopropyl, butyl, tert-butyl, pentyl, hexyl, and the like. Preferred alkyl groups contain from 1 to about 6 carbon atoms ($C_{1-6}$ alkyl).

The term "aryl group" is intended to mean a group derived from an aromatic hydrocarbon by removal of a hydrogen from the aromatic system. Preferred aryl groups contain phenyl or substituted phenyl groups. Thus, the term "aryl" includes an aromatic carbocyclic radical having a single ring or two condensed rings. This term includes, for example, phenyl or naphthyl.

The term "heteroaryl" refers to aromatic ring systems of five or more atoms (e.g., five to ten atoms) of which at least one atom is selected from O, N and S, and includes for example furanyl, thiophenyl, pyridyl, indolyl, quinolyl and the like.

The term "acyl group" is intended to mean a group having the formula RCO—, wherein R is an alkyl group or an aryl group.

The term "alkenyl" refers to a straight or branched chain alkyl moiety having two or more carbon atoms (e.g., two to six carbon atoms, $C_{2-6}$ alkenyl) and having in addition one double bond, of either E or Z stereochemistry where applicable. This term would include, for example, vinyl, 1-propenyl, 1- and 2-butenyl, 2-methyl-2-propenyl, etc.

The term "cycloalkyl" refers to a saturated alicyclic moiety having three or more carbon atoms (e.g., from three to six carbon atoms) and which may be optionally benzofused at any available position. This term includes, for example, cyclopropyl, cyclobutyl, cyclopentyl, cyclohexyl, indanyl and tetrahydronaphthyl.

The term "heterocycloalkyl" refers to a saturated heterocyclic moiety having three or more carbon atoms (e.g., from three to six carbon atoms) and one or more heteroatom from the group N, O, S (or oxidised versions thereof) and which may be optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having three or more carbon atoms (e.g., from three to six carbon atoms) and having in addition one double bond. This term includes, for example, cyclopentenyl or cyclohexenyl.

The term "heterocycloalkenyl" refers to an alicyclic moiety having from three to six carbon atoms and one or more heteroatoms from the group N, O, S (or oxides thereof) and having in addition one double bond. This term includes, for example, dihydropyranyl.

The term "halogen" means a halogen of the periodic table, such as fluorine, chlorine, bromine, or iodine.

The term "optionally substituted" means optionally substituted with one or more of the aforementioned groups (e.g., alkyl, aryl, heteroaryl, acyl, alkenyl, cycloalkyl, heterocycloalkyl, cycloalkenyl, heterocycloalkenyl, or halogen), at any available position or positions.

The term "extracted" is intended to mean that the compound is isolated from all or at least some of the components that accompany it in nature. The term "isolated" is inclusive of "extracted" and is intended to mean that the compound is isolated from all or at least some of the components that accompany it in nature or in its synthesis. For example, according to methods of the present invention, the polyphenolic compounds can be administered or contacted to cells in vivo or in vitro, wherein the compound is in an isolated or non-isolated form, and with or without carriers, diluents, or additional agents.

The term "isomer" is intended to mean a compound that has the same molecular formula as another compound. All isomers fall into either of two groups: structural isomers or stereoisomers.

The term "stereoisomer" is intended to mean a compound that has its atoms joined in the same order as another compound but differs in the way its atoms are arranged in space. Stereoisomers can be subdivided into two categories: enantiomers and diastereomers.

The term "enantiomer" is intended to mean a stereoisomer that is related like an object and its mirror reflection. Enantiomers occur only with compounds whose molecules are chiral, that is, with molecules that are not superposable on their mirror reflections. Separate enantiomers rotate the plane of polarized light and are said to be optically active. They have equal but opposite specific rotations.

The term "racemic" is intended to mean an equimolar mixture of enantiomers.

The term "optical purity" is intended to mean an indication of the purity of a single enantiomer in an optically active substance. A sample of an optically active substance that consists of a single enantiomer is said to be 100% optically pure. An optically active substance that contains less than 100% optical purity contains more than a single enantiomer.

The term "analog" is intended to mean a compound that is similar or comparable, but not identical, to a reference compound, i.e. a compound similar in function and appearance, but not in structure or origin to the reference compound. For example, the reference compound can be a reference green tea polyphenol and an analog is a substance possessing a chemical structure or chemical properties similar to those of the reference green tea polyphenol. As used herein, an analog is a chemical compound that may be structurally similar to another but differs in composition (as in the replacement of one atom by an atom of a different element or in the presence of a particular functional group). An analog may be extracted from a natural source or be prepared using synthetic methods.

The term "cancer" is intended to mean any cellular malignancy whose unique trait is the loss of normal controls which results in unregulated growth, lack of differentiation and ability to invade local tissues and metastasize. Cancer can develop in any tissue of any organ. More specifically, cancer is intended to include, without limitation, prostate cancer, leukemia, hormone dependent cancers, breast cancer, colon cancer, lung cancer, epidermal cancer, liver cancer, esophageal cancer, stomach cancer, cancer of the brain, and cancer of the kidney.

The terms "treatment", "treating" and the like are intended to mean obtaining a desired pharmacologic and/or physiologic effect, e.g., inhibition of cancer cell growth or induction of apoptosis of a cancer cell. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition (e.g., preventing cancer) from occurring in an individual who may be predisposed to the disease but has not yet been diagnosed as having it; (b) inhibiting the disease, (e.g., arresting its development); or (c) relieving the disease (e.g., reducing symptoms associated with the disease).

The term "anti-cancer activity" is intended to mean an activity which is able to substantially inhibit, slow, interfere, suppress, prevent, delay and/or arrest a cancer and/or a metastasis thereof (such as initiation, growth, spread, and/or progression thereof of such cancer and/or metastasis).

The term "biological activity" is intended to mean having the ability to inhibit chymotrypsin-like activity of the proteasome. Biological activity is also intended to mean having the ability to inhibit cell growth, induce apoptosis, and/or suppress the transforming activity in cancer cells.

The term "natural compound" is intended to mean a compound extractable from a natural source.

The term "administering" and "administration" is intended to mean a mode of delivery including, without limitation, oral, rectal, parenteral, subcutaneous, intravenous, intramuscular, intraperitoneal, intraarterial, transdermally or via a mucus membrane. The preferred one being orally. One skilled in the art recognizes that suitable forms of oral formulation include, but are not limited to, a tablet, a pill, a capsule, a lozenge, a powder, a sustained release tablet, a liquid, a liquid suspension, a gel, a syrup, a slurry, a suspension, and the like. For example, a daily dosage can be divided into one, two or more doses in a suitable form to be administered at one, two or more times throughout a time period.

The term "therapeutically effective" is intended to mean an amount of a compound sufficient to substantially improve some symptom associated with a disease or a medical condition. For example, in the treatment of cancer, a compound which decreases, prevents, delays, suppresses, or arrests any symptom of the disease would be therapeutically effective. A therapeutically effective amount of a compound is not required to cure a disease but will provide a treatment for a disease such that the onset of the disease is delayed, hindered, or prevented, or the disease symptoms are ameliorated, or the term of the disease is changed or, for example, is less severe or recovery is accelerated in an individual.

The term "chymotrypsin-like activity" refers to the ability of the eukaryotic proteasome β subunit to cleave amino acid sequences after hydrophobic residues, and is intended to include chymptrypsin activity.

The polyphenolic compounds of the present invention may be used in combination with either conventional methods of treatment and/or therapy or may be used separately from conventional methods of treatment and/or therapy.

When the compounds of this invention are administered in combination therapies with other agents, they may be administered sequentially or concurrently to an individual. Alternatively, pharmaceutical compositions according to the present invention may be comprised of a combination of a compound of the present invention, as described herein, and another therapeutic or prophylactic agent known in the art.

It will be understood that a specific "effective amount" for any particular in vivo or in vitro application will depend upon a variety of factors including the activity of the specific compound employed, the age, body weight, general health, sex, and/or diet of the individual, time of administration, route of administration, rate of excretion, drug combination and the severity of the particular disease undergoing prevention or therapy. For example, the "effective amount" may be the amount of polyphenol compound of the invention necessary to achieve inhibition (e.g., diminishment or abatement) of proteosomal chymotrypsin-like activity in vivo or in vitro. The "effective amount" may be the amount of polyphenol compound of the invention necessary to achieve apoptosis or an increase in the relative number of $G_1$ cells.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include citric acid, lactic acid, tartaric acid, fatty acids, and the like.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

As used herein, the term "pharmaceutically acceptable carrier" includes any and all solvents (such as phosphate buffered saline buffers, water, saline), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients can also be incorporated into the compositions. The pharmaceutical compositions of the subject invention can be formulated according to known methods for preparing pharmaceutically useful compositions. Formulations are described in a number of sources which are well known and readily available to those skilled in the art. For example, *Remington's Pharmaceutical Science* (Martin E W (1995) Easton Pa., Mack Publishing Company, $19^{th}$ ed.) describes formulations which can be used in connection with the subject invention.

As used herein, the terms "individual" and "patient" are used interchangeably to refer to any vertebrate species, such as humans and animals. Preferably, the patient is of a mammalian species. Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Human or non-human animal patients can range in age from neonates to elderly.

Materials and Methods

Materials. Highly purified tea polyphenols (−)-EGCG (>95%), (−)-GCG (>98%), (−)-ECG (>98%), (−)-CG (>98%), fetal calf serum, propidium iodide, 3-[4,5-dimethylthiazol-2-yl]-2,5-diphenyltetrazolium bromide (MTT), RNase A, and DMSO were purchased from Sigma (St. Louis, Mo.). (+)-EGCG, benzyl-protected-(+)-EGCG, (+)-GCG, (−)-EGCG-amide, and (+)-EGCG-amide were prepared by enantioselective synthesis (see below). Purified 20S eukaryotic proteasome from rabbit was purchased from BOSTON BIOCHEM (Cambridge, Mass.). Purified 20S prokaryotic proteasome (*Methanosarcina thermophile*, Recombinant, *E. coli*) was purchased from CALBIOCHEM (La Jolla, Calif.). Fluorogenic peptide substrates Suc-Leu-Leu-Val-Tyr-AMC (for the proteasomal chymotrypsin-like activity) was obtained from Calbiochem (La Jolla, Calif.). RPMI 1640 medium, Dulbecco's modified Eagle's medium, MEM non-essential amino acids solution, MEM-sodium pyruvate solution, penicillin, and streptomycin were from INVITROGEN (Carlsbad, Calif.). Monoclonal antibody to $p27^{Kip}$ was purchased from PHARMINGEN (San Diego, Calif.); polyclonal antibodies to IκB-a, Bax and actin, and monoclonal antibody to ubiquitin were from SANTA CRUZ Biotechnology Inc. (Santa Cruz, Calif.).

Inhibition of purified 20S proteasome activity by natural or synthetic GTPs. Purified prokaryotic (0.5 μg) or eukaryotic (0.02 μg) 20S proteasome was incubated with 20 μM fluorogenic peptide substrate, Suc-Leu-Leu-Val-Tyr-AMC for 30 mM at 37° C. in 100 μl of assay buffer (50 mM Tris-HCl, pH 7.5), with or without a natural or synthetic tea polyphenol. After incubation, production of hydrolyzed 7-amido-4-methyl-coumarin (AMC) groups was measured using a multi-well plate VERSAFLUOR Fluorometer with an excitation filter of 380 nm and an emission filter of 460 nm (BIO-RAD), and a multi-well plate reader Wallac 1420 VICTOR™[2] with an excitation filter of 355 nm and an emission filter of 460 nm (EG&G WALLAC).

Assays for irreversible inhibition. To measure the effect of dialysis on (−)-EGCG-mediated proteasome inhibition, 20S prokaryotic proteasome (2 μg) was incubated with 10 (−)-EGCG or the control solvent ($H_2O$) in 50 mM Tris-HCl, pH 7.5 for 1 hour. This was then incubated at 4° C. either without or with dialysis overnight using a 10,000 MWCO Pierce Slide-A-Lyzer Dialysis Cassette (Rockford, Ill.) in a rotating bath of 50 mM Tris-HCl, pH 7.5. The proteasomal chymotrypsin-like activity was then assayed as previously described. As a control, an EGCG solution (without purified 20S proteasome) was dialyzed overnight, followed by measurement of the effects on inhibition of the proteasome activity.

Molecular modeling and docking studies. The crystal structure of the eukaryotic yeast 20S proteasome was obtained from the Protein Database (Ref. Number 1JD2), and used for the docking examples. The yeast 20S proteasome is structurally very similar to the mammalian 20S proteasome, and the chymotrypsin active site between the two species is highly conserved.

The AutoDock suite of programs, which was used for the docking calculations, employs an automated docking approach allowing ligand flexibility as described to a full extent elsewhere. AutoDock has been compared to various docking programs in several studies and has consistently produced docked conformations that predict X-ray crystal structures with bound ligands. Default parameters were used as is described in the AutoDock manual except for those changes mentioned below. The dockings were run on an i386 architecture computer running Redhat Linux 6.0.

The crystal structure of the 20S proteasome and the ligands were prepared for docking by following the default protocols except were noted. The energy-scoring grid was prepared as a 20×20×20 Å box centered around the β5 catalytic N-terminal threonine, and the ligand was limited to this search space during docking. Atomic solvation parameters were assigned to the proteasome using default parameters. The default parameters for the Lamarckian genetic algorithm were used as the search protocol except for the maximum number of energy evaluations, which were changed to 5 million. This Lamarckian genetic algorithm method with AutoDock has previously been shown to reproduce binding modes very similar to crystal structures with bound ligands. AutoDock relies upon an empirical scoring function that provides approximate binding free energies. The default parameters were kept for mutation, crossover and elitism. The pseudo-Solis and Wets local search method was included as default parameters as well.

Docking modes were selected based on two criteria: their proximity to the N-terminal threonine and placement of the ring system of the molecule within the S1 hydrophobic pocket. Of the orientations/conformations that fit these two criteria, the docked structure of lowest free energy was chosen. Each molecule was docked with up to 30 runs of 5 million energy evaluations for each run. The output from AutoDock and all modeling studies as well as images were produced with PyMOL. PyMOL was used to calculate the distances of hydrogen bonds as measured between the hydrogen and its respective atom.

Determination of nucleophilic susceptibility. The electron density surface colored by nucleophilic susceptibility was created by performing Extended Hückel molecular orbital calculations using Cache Worksystem ver. 3.2 (Oxford Molecular Ltd., now Accelrys). A colored "bull's-eye" with a white-center denotes atoms that are highly susceptible to nucleophilic attack.

Cell Culture, Cell Extract Preparation, and Western Blot Assay. Human leukemia Jurkat T and prostate cancer LNCaP cells were cultured in RPMI 1640 medium supplemented with 10% fetal calf serum, 100 units/ml of penicillin, and 100 μg/ml streptomycin. Human immortalized, non-transformed NK cells (YT cell line) (38) were cultured in RPMI 1640 supplemented with 1 mM MEM sodium pyruvate solution, 0.1 mM MEM non-essential amino acids solution, 10% fetal calf serum. 100 units/ml penicillin, and 100 μg/ml streptomycin. Normal (WI-38) and simian virus 40 (SV40)-transformed (VA-13) human fibroblasts were grown in Dulbecco's modified Eagle's medium supplemented with 10% fetal calf serum, 100 units/ml of penicillin and 100 μg/ml of streptomycin. All cells were maintained at 37° C. in a humidified incubator with an atmosphere of 5% $CO_2$. A whole cell extract was prepared in accordance with An et al. (An, B. et al. *Cell Death Differ*, 1998, 5:1062-75). Briefly, cells were harvested, washed with PBS twice, and homogenized in a lysis buffer [50 mM Tris-HCl (pH 8.0), 5 mM EDTA, 150 mM NaCl, 0.5% NP-40, 0.5 mM phenylmethylsulfonyl fluoride, and 0.5 mM dithiothreitol] for 30 min at 4° C. Afterwards, lysates were centrifuged at 12,000×g for 15 min at 4° C., and the supernatants were collected as whole cell extracts. Equal amounts of protein extract (60 μg) were resolved by SDS-polyacrylamide gel electrophoresis and transferred to a nitro-cellulose membrane using a Semi-Dry Transfer system (BIO-RAD, Hercules, Calif.). Jurkat T, LNCaP, or DU-145 cells were treated with various concentrations of synthetic or natural tea polyphenols for indicted hours. The enhanced chemi-luminescence (ECL) Western blot analysis was then performed using specific antibodies to the proteins of interest ($p^{27}$kip, IκB-a, PARP, Bax or actin). The ratio of p27 or IκB-α to the corresponding actin was determined by scanning intensities of the protein bands.

Flow Cytometry. Cell cycle analysis based on DNA content was performed as in An et al. (An, B. et al. *Cell Death Differ,* 1998, 5:1062-75). At each time point, cells were harvested, counted, and washed twice with PBS. Cells ($5 \times 10^6$) were suspended in 0.5 ml PBS, fixed in 5 ml of 70% ethanol overnight at −20° C., centrifuged, resuspended again in 1 ml of propidium iodide staining solution (50 μg propidium iodide, 100 units RNase A and 1 mg glucose per ml PBS), and incubated at room temperature for 30 minutes. The cells were then analyzed with FACScan (Becton Dickinson Immunocytometry, CA), ModFit LT and WinMDI V.2.8 cell cycle analysis software (Verity Software; Topsham, Me.). The cell cycle distribution is shown as the percentage of cells containing $G_1$, S, $G_2$, and M phase DNA judged by propidium iodide staining. The apoptotic population is determined as the percentage of cells with sub-$G_1$ DNA content (<$G_1$).

Soft Agar Assay. The soft agar assay was performed according to Smith et al. (Smith, D. M. et al. *Mol Med,* 2002, 8:382-392) with a few modifications. In brief, in a six-well plate, a bottom feeder layer (0.6% agar) was prepared with DMEM media containing 10% fetal bovine serum, 100 units/ml penicillin, and 100 μg/ml streptomycin. A top layer (0.3% agar) was prepared with DMEM and the same media as described above but containing $2 \times 10^4$ prostate cancer LNCaP cells and indicated analogs or DMSO as a control. Plates were incubated at 37° C. in 5% $CO_2$ in a humidified incubator for two weeks. MTT (1 mg/ml) was added to each well and incubated overnight to allow complete formation of purple formazan crystals. The plates were then scanned and photographed, and the number of colonies was quantified by QUANTITY ONE v.4.0.3 software (Bio-Rad, Hercules, Calif.).

Example 1

(+)-EGCG-amide and (−)-EGCG-amide Potency for Proteasomal Inhibition

Purified prokaryotic (0.5 μg) or eukaryotic (0.02 μg) 20S proteasome was incubated with 20 μM fluorogenic peptide substrate, Suc-Leu-Leu-Val-Tyr-AMC for 30 minutes at 37° C. in 100 μl of assay buffer (50 nM Tris-HCl, pH 7.5), with or without a natural or synthetic tea polyphenol. After incubation, production of hydrolyzed AMC groups was measured using a multi-well plate VERSAFLUOR Fluorometer with an excitation filter of 380 nm and an emission filter of 460 nm.

The $IC_{50}$ values against 20S eukaryotic proteasome were determined to be 320 and 405 nM for both (−)-EGCG-amide and (+)-EGCG-amide, respectively (FIGS. 4C and 4D). Compared to (−)- and (+)-EGCG, both amide compounds have decreased proteasome-inhibitory potencies respectively (FIGS. 4C and 4D vs. FIGS. 3A and 3B) although their stereochemical structures were not changed (FIG. 1).

Example 2

Figures 9A, 9B:
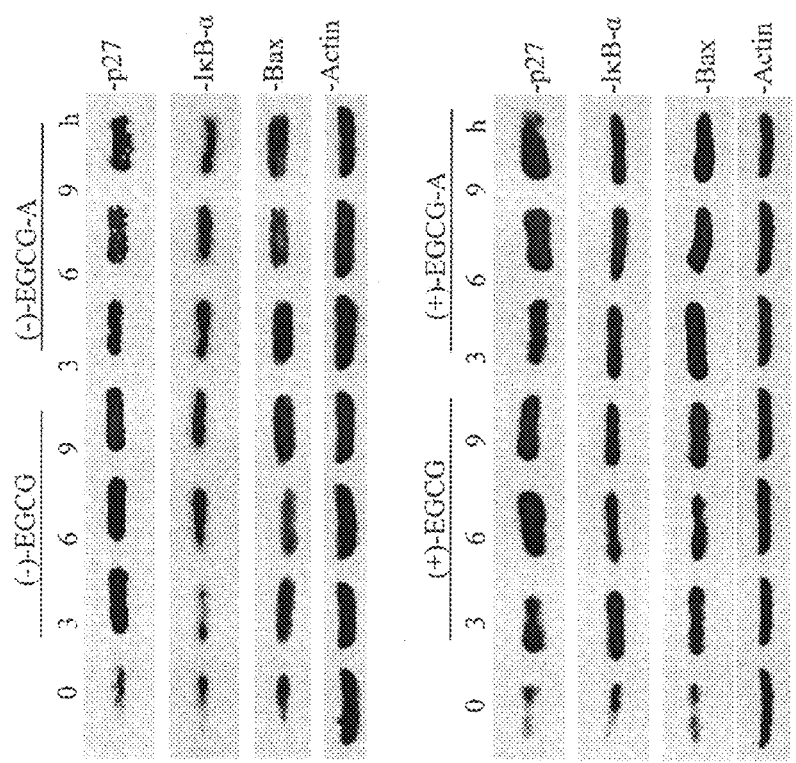
FIG. 9A shows the accumulation of p27, IκB-a, and Bax proteins by (−)-EGCG and (−)-EGCG-amide.
FIG. 9B shows the accumulation of p27, IκB-a, and Bax proteins by (+)-EGCG and (+)-EGCG-amide.

Inhibition of the Proteasomal Activity by Synthetic EGCG-Amides in Intact Prostate Cancer Cells To investigate whether (−)-EGCG-amide and (+)-EGCG-amide inhibit intact tumor cell proteasome activity, human prostate cancer LNCaP cells were treated with 25 μM of (−)- or (+)-EGCG-amide for up to 9 hours, followed by measurement of p27, IκB-a and Bax, three well-known proteasome target proteins (Pagano, M. et al. *Science,* 1995, 269:682-685; An, B. et al. *Cell Death Differ,* 1998, 5:1062-75; Sun, J. et al. *Cancer Res,* 2001, 61:1280-1284; Palombella, V. J. et al. *Cell,* 1994, 78:773-785; Thompson, J. E. et al. *Cell,* 1995, 80:573-582; Perkins, N. D. *Trends Biochem Sci,* 2000, 25:434-440; Chang, Y. C. et al. *Cell Growth Differ,* 1998, 9:79-84; Li, B. and Dou, Q. P. *Proc Natl Acad Sci USA,* 2000, 97:3850-3855; Nam, S. et al. *Cancer Epidemiol Biomarkers Prev,* 2001, 10:1083-1088). In this experiment (−)-EGCG and (+)-EGCG were used as positive controls. Similar to (−)-EGCG and (+)-EGCG, the two corresponding EGCG amides were able to increase levels of p27, IκB-a and Bax by 3 hours, which remained high up to 9 hours (FIGS. 9A-9B). Both (−)- and (+)-EGCG-amide were also able to inhibit the proteasome activity in human breast cancer MCF-7 cells. This demonstrates that EGCG amides are capable of inhibiting the proteasome chymotrypsin-like activity in intact tumor cells.

Example 3

Synthetic EGCG Analogs with Double Ester or Amide Bonds Inhibit the Chymotrypsin-Like Activity of Purified 20S Proteasome To further study the functional roles of the ester or amide bond of EGCG compounds in inhibiting the proteasomal activity, several GTP analogs containing an additional ester bond between B- and C-rings were designed. To overcome the stability problem, the C-ring oxygen was replaced by the isosteric $CH_2$ group (FIG. 8). These compounds, named GTP-1 to −5 (FIG. 8), were synthesized and tested for proteasome-inhibitory activity.

Potencies of three analogs without the A-ring, GTP-1, -2 and -3 were investigated first. GTP-1 with cis-diesters has an $IC_{50}$ value of 1.9 μM against the chymotrypsin-like activity of purified 20S proteasome (FIG. 8). GTP-2 containing cis-diamides has an $IC_{50}$ value of 2.5 μM, which is slightly less potent than GTP-1. GTP-3 with trans-diamides has an $IC_{50}$ value of 1.5 μM (FIG. 8). The decreased potencies of GTP-1, -2 and -3, compared to that of the natural (−)-EGCG ($IC_{50}$ 0.1-0.2 μM; 17, 36), suggest that the A-ring is required for inhibiting the proteasome activity.

To further examine the A-ring requirement, the potencies of the two "A-C-ring" analogs, GTP-4 and GTP-5, was measured. GTP-4 contains cis-diesters and has $IC_{50}$ of 0.34 μM (FIG. 8). Addition of a hydroxyl group to the A-ring of GTP-4 generates GTP-5 (FIG. 8), whose $IC_{50}$ was found to be 0.73 μM. Compared to GTP-1, -2 and -3, GTP-4 and -5 compounds have increased potencies, consistence with the requirement of the A-ring for proteasome inhibition.

Example 4

Accumulation of Proteasome Target and Polyubiquitinated Proteins and Induction of $G_1$ Arrest and Cell Death by GTP Analogs Having determined that the synthetic GTP-1 to −5 analogs are able to inhibit the proteasomal chymotrypsin-like activity in vitro (FIG. 8), these compounds were investigated for their potency in inhibiting intact tumor cellular proteasome activity. To do so, human prostate cancer LNCaP cells were treated with one of these compounds for the indicated hours, followed by measuring levels of proteasome target proteins, p27, IκB-a, and Bax, and polyubiquitinated proteins.

Figure 10A:
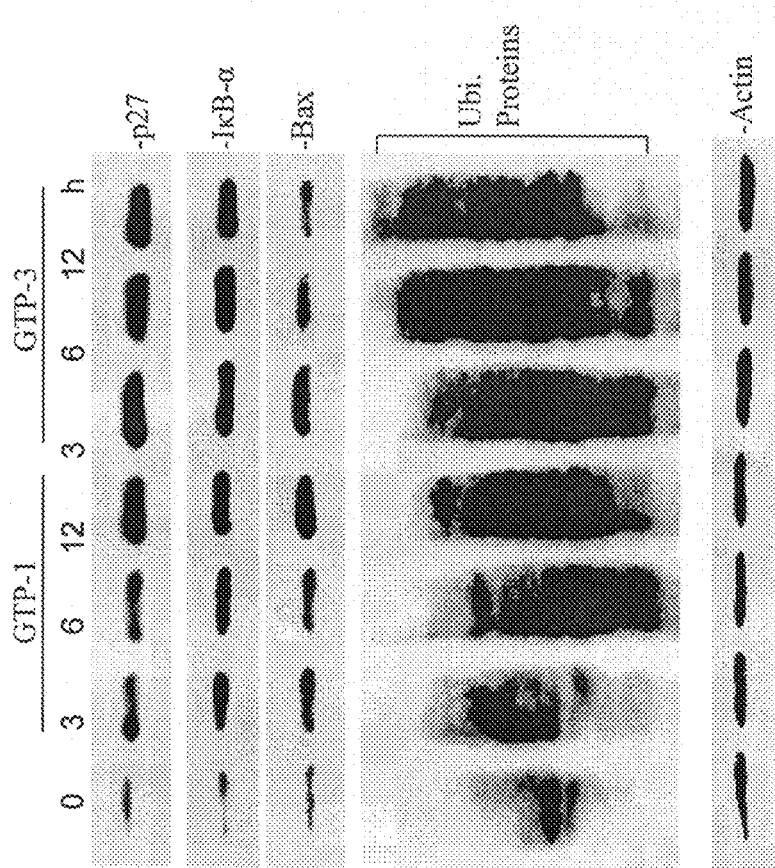
FIG. 10A shows the accumulation of p27, IκB-a, Bax, and ubiquitinated proteins by GTP-1 and GTP-3.

Treatment of LNCaP cells with 50 μM of GTP-1 increased levels of p27, IκB-a, and Bax proteins at as early as 3 hours, which were significantly increased at 12 hours (FIG. 10A). Inhibition of proteasome activity by GTP-1 should also increase the levels of polyubiquitinated proteins, because most of the proteasome-mediated protein degradation pathways require ubiquitination (Adams, J. et al. *Cancer Res,* 1999, 59:2615-2622; Dou, Q. P. and Li, *B Drug Resist Updat,* 1999, 2:215-223; Almond, J. B. and Cohen, G. M. *Leukemia,* 2002, 16:433-443; Kisselev, A. F. and Goldberg, A. L. *Chem Biol,* 2001, 8:739-758). Indeed, GTP-1 treatment also caused accumulation of polyubiquitinated proteins, with the highest levels at 12 hours (FIG. 10A). As a control, expression of actin protein was relatively unchanged during the treatment (FIG. 10A).

GTP-3 was more potent than GTP-1 when tested in LNCaP cells (FIG. 10A). Treatment with GTP-3 for 3 hours greatly increased levels of p27, IκB-a, and ubiquitinated proteins, which remained high or further increased for 12 hours (FIG. 10A). GTP-3 transiently increased levels of Bax protein with the highest value at 3 hours (FIG. 10A). These results support the conclusion that amide compounds are stable and potent proteasome inhibitors in vivo.

Figure 10B:
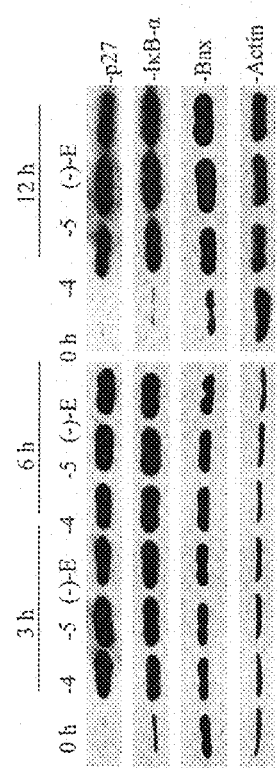
FIG. 10B shows a Western blot assay using specific antibodies to p27, IκB-a, Bax, and ubiquitinated proteins for GTP-4, GTP-5 and (−)-EGCG.

In another kinetic experiment, treatment of LNCaP cells with 50 μM of GTP-4 or GTP-5 resulted in a significant increase in levels of p27 and IκB-a, with potency similar to that of (−)-EGCG (FIG. 10B). In this experiment, levels of Bax protein were increased only at 12 hours by GTP-4, GTP-5 or (−)-EGCG (FIG. 10B). This result demonstrates that both GTP-4 and GTP-5 are potent proteasome inhibitors in intact tumor cells.

Figures 11A, 11B:
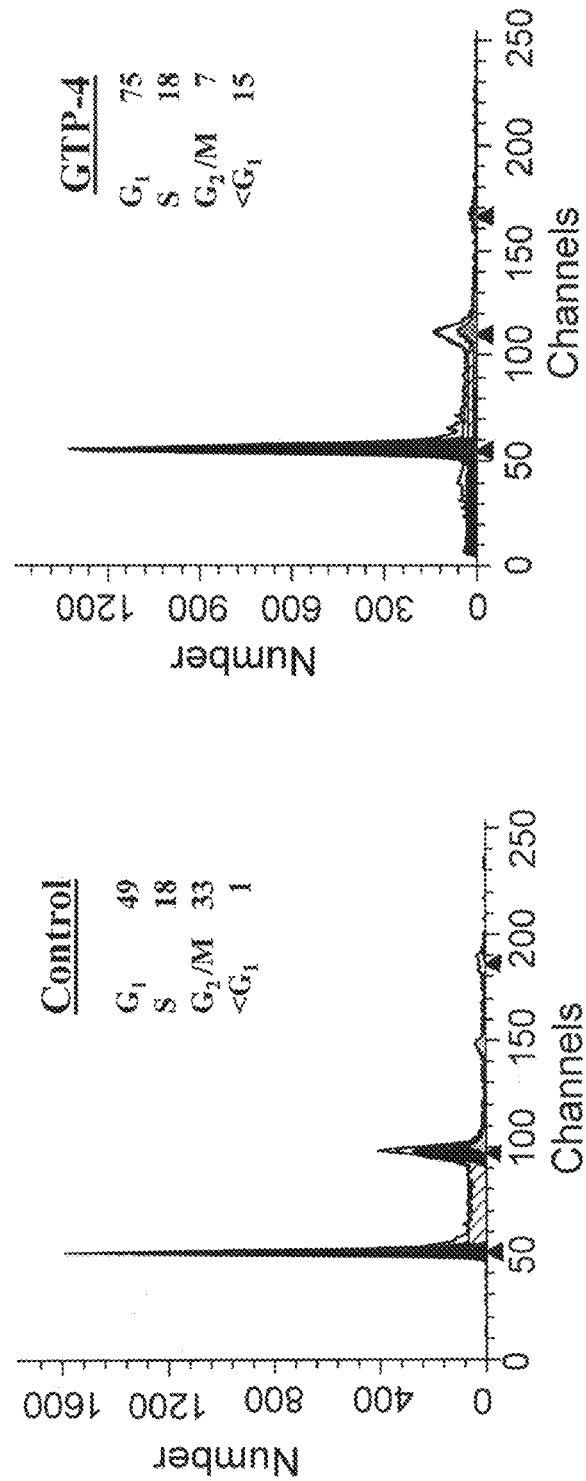
FIG. 11A shows a DNA histogram for a control.
FIG. 11B shows a DNA histogram for GTP-4.
Figure 11C:
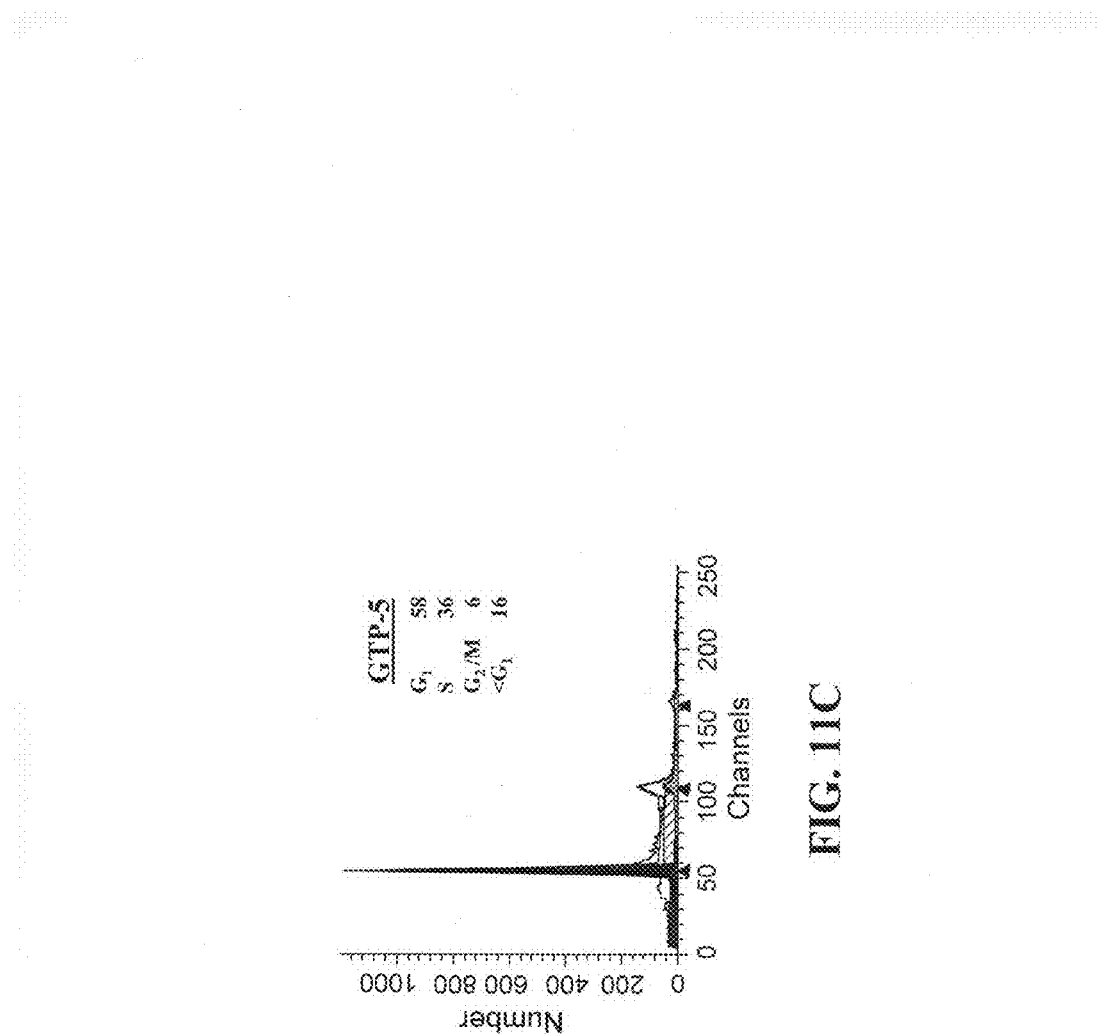
FIG. 11C shows a DNA histogram for GTP-5.

Previous studies have shown that overexpression of p27 (Pagano, M. et al. *Science,* 1995, 269:682-685), IκB-a (Verma, I. M. et al. *Genes Dev,* 1995, 9:2723-2735), and Bax (Li, B. and Dou, Q. P. *Proc Natl Acad Sci USA,* 2000, 97:3850-3855) results in $G_1$ arrest or apoptosis. If increased levels of these proteasome target proteins by the synthetic EGCG analogs are functional, growth inhibition of tumor cells would be expected. To test this possibility, GTP-4 and GTP-5 were selected, which showed significant potency both in vitro and in vivo (FIGS. 8, 10A, and 10B), to treat human Jurkat T cells for 24 hours, followed by flow cytometry analysis. The $G_1$ population was indeed increased by 26% and 9% by treatment with GTP-4 and GTP-5, respectively (FIG. 11). Both compounds also increased the sub-G1 DNA cell population by ~15% (FIG. 11), indicating the occurrence of DNA fragmentation and cell death.

Example 5

Synthetic EGCG Analogs Inhibit Colony Formation of Prostate Cancer Cells

Figure 12B:
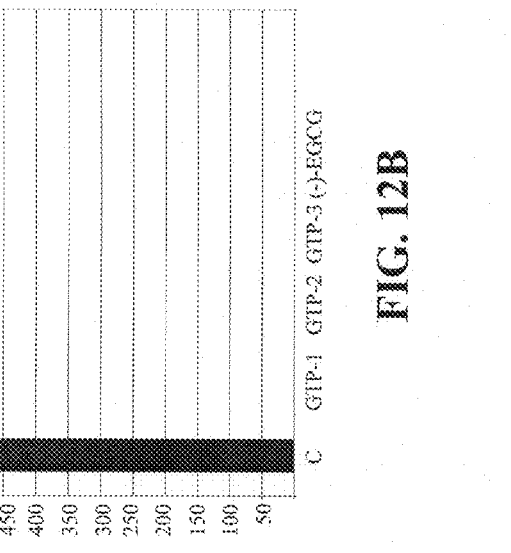
FIG. 12B shows a bar graph of the mean number of colonies present in each treatment plate.
Figure 12A:
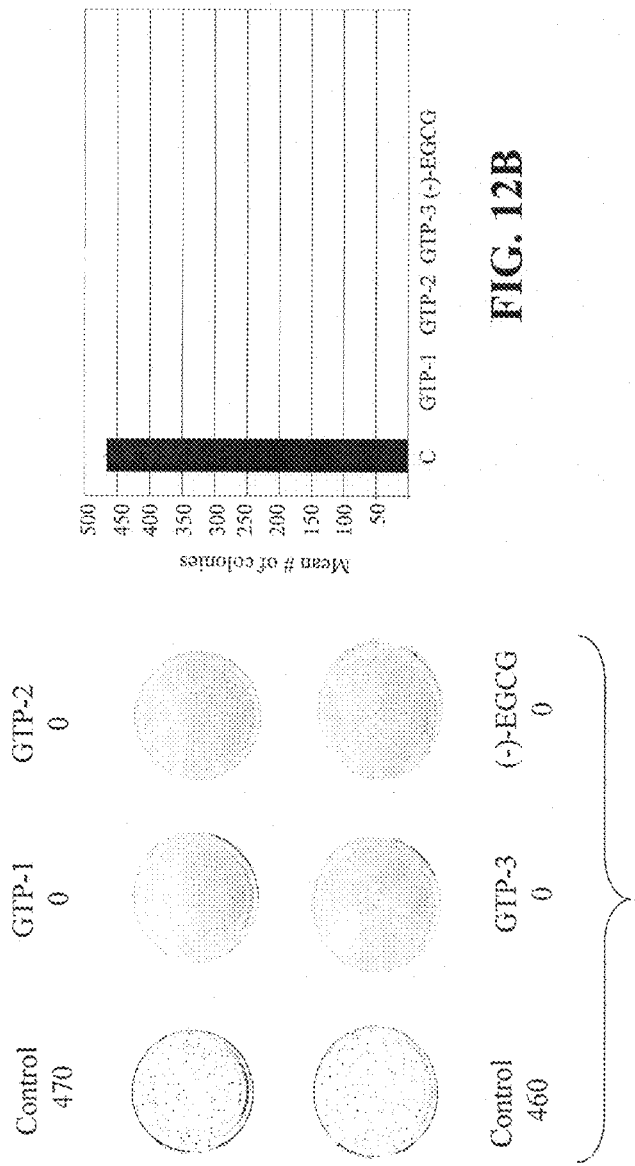
FIG. 12A shows soft agar colony formation of prostate cancer cells in the present of a control, GTp-1, GTP-2, GTP-3, and (−)-EGCG.

The in vivo effects of several GTP analogs were investigated with a soft agar assay that measures the transforming activity of human tumor cells. LNCaP cells were plated in soft agar (see Materials and Methods) along with 50 μM of GTP-1, -2, -3, (−)-EGCG (as a positive control; Smith, D. M. et al. *Mol Med,* 2002, 8:382-392, 2002), or the solvent (as a negative control), followed by a 14 day-incubation to allow for colony formation (FIGS. 12A and 12B). The solvent-treated plates allowed for the development of ~500 colonies, while treatment with GTP-1, -2 or -3 completely blocked LNCaP transformation capability, with potency similar to that of natural (−)-EGCG (FIGS. 12A and 12B). These data suggest that although GTP-1, -2 and -3 are less potent in vitro than (−)-EGCG (FIG. 8), these analogs are potent in vivo.

Figure 21A:
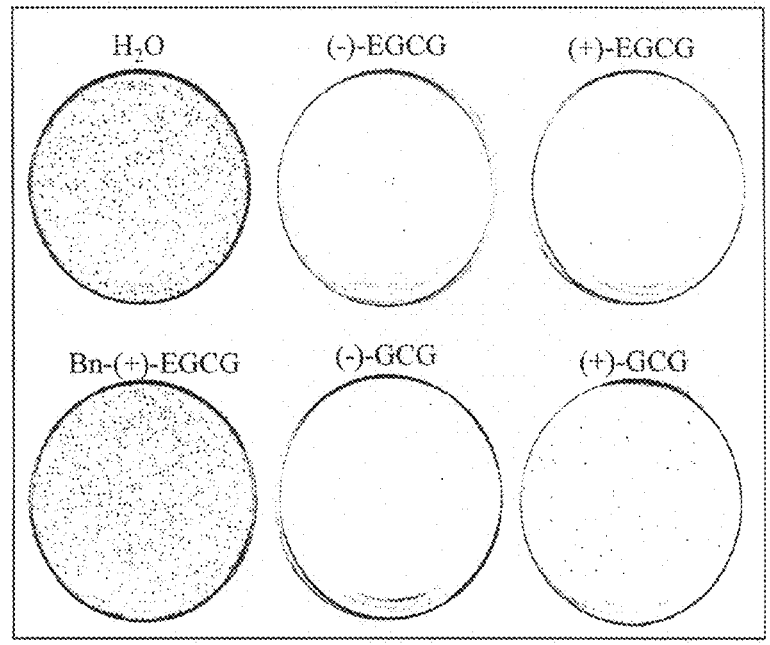
FIG. 21A shows colony growth in the presence of synthetic and natural GTPs.
Figure 21B:
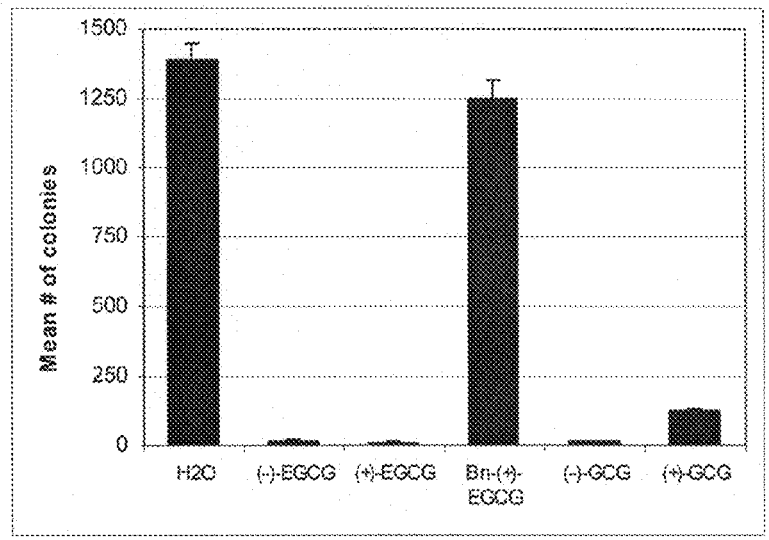
FIG. 21B shows a bar graph of the mean number of colonies grown in the presence of synthetic and natural GTPs.

In a second experiment, LNCaP cells were plated in soft agar along with 10 μM of each indicated GTP or solvent ($H_2O$), followed by a 14 day-incubation to allow for colony formation (FIG. 21A). The solvent-treated plates allowed for the development of ~4,400 colonies, while synthetic (+)-EGCG treatment abolished formation of nearly all the colonies (99.5% inhibition), similar to the natural (−)-EGCG (99.0% inhibition; FIGS. 21A and 21B). As expected, the inactive synthetic Bn-(+)-EGCG, which cannot inhibit the proteasome activity (FIGS. 16A, 17A, 17B, and 17C), had little inhibitory activity on colony formation (~10% inhibition). The synthetic (+)-GCG compound was found to inhibit 91.5% of colony formations, however, it was not as potent as the synthetic (+)-EGCG or the natural (−)-GCG (99% inhibition; FIGS. 21A and 21B). Colonies were quantified with an automated counter and presented as mean values from triplicate independent experiments. Error bars denote standard deviations. These data demonstrate that synthetic GTPs, especially (+)-EGCG, can inhibit prostate cancer cell growth and colony formation in a semi-in situ assay.

Example 6

Figure 13C:
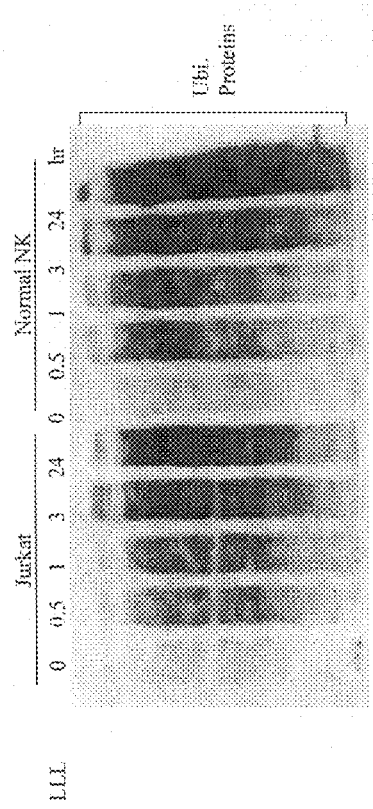
FIG. 13C shows a Western blot assay using specific antibodies to p27, IκB-a, ubiquitin, and actin.

Synthetic EGCG Analogs Induce Accumulation of Proteasome Target Proteins Preferentially in Tumor and Transformed Over Normal and Non-Transformed Cells Immortalized, non-transformed normal natural killer (NK) cells (YT line) (Drexler, H. G. et al. *Leuk Res,* 2000, 24:881-911) and human leukemic Jurkat T cells (as a control) were treated with either (−)-EGCG (as a comparison) or (−)-EGCG-amide for up to 12 hour. Levels of IκB-α protein were significantly increased in Jurkat T cells by either (−)-EGCG or its amide (up to 6- and 8-fold, respectively, at 6 hours; FIGS. 13A and 13B). In contrast, IκB-α expression in non-transformed NK cells was unchanged during each treatment, although the basal level (and the mobility) of IκB-α protein was higher in NK cells (FIGS. 13A and 13B). Levels of p27 in Jurkat cells were increased by 17-fold after (−)-EGCG treatment; no p27 expression was detected in NK cells, even after treatment (FIG. 13A). These data support the conclusion that EGCG analogs can inhibit the proteasome activity selectively in tumor over non-transformed cells (Nam, S. et al. *J Biol Chem,* 2001, 276:13322-13330).

When the selectivity of the commercial tripeptidyl proteasome inhibitor LLL was investigated, increased levels of ubiquitinated proteins with similar kinetics in both Jurkat and NK cells were found (FIG. 13C), suggesting non-tumor selectivity. Therefore, EGCG analogs have greater selectivity than LLL in leukemic Jurkat T over non-transformed NK cells.

Figures 14A, 14B:
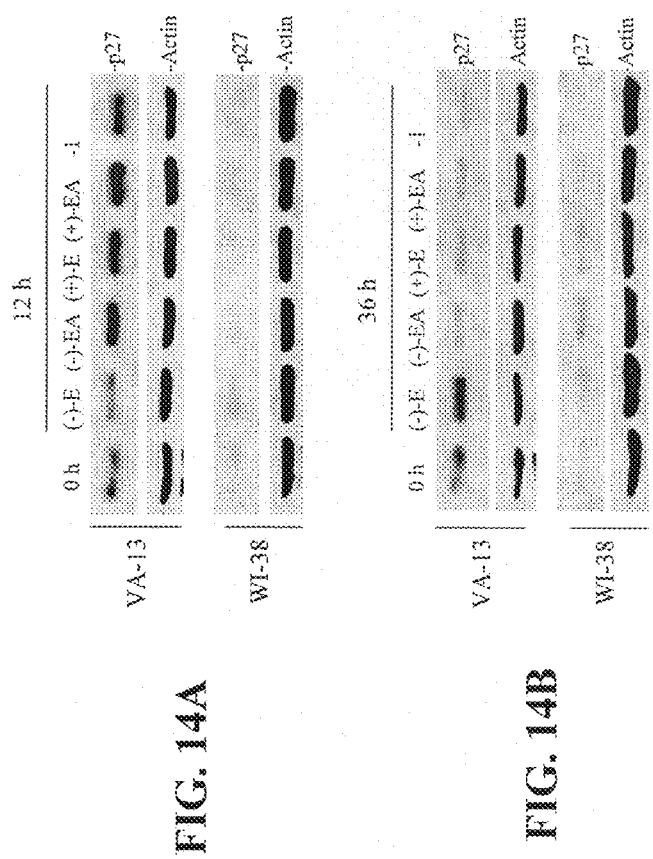
FIG. 14A shows the preferable accumulation of p27 by (−)-EGCG-A, (+)-EGCG, (+)-EGCG-A, and GTP-1 in the transformed over the normal human fibroblasts at twelve hours.
FIG. 14B shows the preferable accumulation of p27 by (−)-EGCG-A, (+)-EGCG, (+)-EGCG-A, and GTP-1 in the transformed over the normal human fibroblasts at twelve hours.

Normal WI-38 and SV40-transformed VA-13 cell lines were treated with 25 μM of (−)-EGCG, (−)-EGCG-amide, (+)-EGCG, (+)-EGCG-amide, or GTP-1 for either 12 hours or 36 hours. It was found that at 12 hours (−)-EGCG, (−)-EGCG-amide, (+)-EGCG, (+)-EGCG-amide, and GTP-1 significantly increased levels of p27 protein, while at 36 hours (−)-EGCG accumulated p27 levels (FIGS. 14A and 14B). In contrast, p27 levels in normal WI-38 cells were slightly increased only by (−)-EGCG-amide, but not any other tested compounds at 36 hours (FIGS. 14A and 14B). These data suggest that the tested EGCG analogs may have the ability to inhibit the proteasome activity preferentially in tumor and transformed cells versus normal or non-transformed cells.

Example 7

Synthesis of Green Tea Polyphenols (GTPs)

A. Enantioselective Synthesis of GTPs $^1$H and $^{13}$C NMR spectra were recorded on Varian 400 or 300 MHz spectrometers. Spectra were referenced to residual chloroform (δ 7.26 ppm, $^1$H; δ 77.0 ppm, $^{13}$C), acetone (δ 2.04 ppm, $^1$H, 29.8 ppm, $^{13}$C) or tetramethylsilane (δ 0.00 ppm, $^1$H and $^{13}$C). Chemical shifts are reported in ppm (δ); multiplicities are indicated by s (singlet), d (doublet), t (triplet), q (quartet), m (multiplet) and br (broad). Coupling constants, J are reported in Hertz. [a]$_D$ were measured on a JASCO DIP-140 Polarimeter. Chemicals were used as obtained from commercial sources unless specified otherwise. THF was freshly distilled over Na/benzophenone and used immediately. CH$_2$Cl$_2$ was freshly distilled over CaH$_2$ and used immediately. trans-5,7-bis-benzyloxy-2-[3,4,5-tris (benzyloxy)phenyl]-chroman-3-ol, and tris(benzyloxy)benzoic acid chloride were prepared by literature methods.

(+)-EGCG and the fully benzyl protected (+)-EGCG [Bn-(+)-EGCG] were prepared according to previously reported procedures.

B. Preparation of (+)-GCG (+)-GCG was prepared according to Smith et al. (Smith, D. M. et al. *Molecular Medicine*, 2002, 8(7):382-392). To a solution of (+)-[2R,3S]-5,7-bis(benzyloxy)-2-[3,4,5-tris (benzyloxy)phenyl]chroman-3-ol (145 mg, 190 μmol, 1.0 equiv) in CH$_2$Cl$_2$ (15 mL) was added dimethylaminopyridine (58 mg, 470 μM, 2.5 equiv) under N$_2$. The solution was cooled to 0° C., and 3,4,5-tris(benzyloxy)benzoic acid chloride (131 mg, 285 μmol, 1.5 equiv) was added. The mixture was allowed to warm to room temperature and stirred for 16 hours. Saturated NaHCO$_3$ aqueous solution (20 mL) was added and the mixture was stirred at room temperature for an additional 1 hours. The layers were separated, and the aqueous layer was extracted with EtOAc (4×25 mL). The combined organic phase was washed with brine (20 mL), dried over Na$_2$SO$_4$, and was concentrated by rotary evaporator and vacuum drying to give crude product which was purified by silica gel chromatography (C$_6$H$_6$/EtOAc=100/1) to afford pure product 195 mg (87%) of the fully benzyl protected gallate ester as a white solid. [a]$_D$=22.17 (c1.09, CHCl$_3$); NMR (300 MHz, CDCl$_3$): 7.31 (m, 42H), 6.70 (s, 2H), 6.32 (s, 1H), 6.31 (s, 1H), 5.48 (m, 1H), 5.12 (m, 1H), 5.01 (m, 16H), 2.99 (dd, J=16.8, 5.2, 1H), 2.84 (dd, J=16.8, 10.2, 1H); $^{13}$C NMR (75 MHz, CDCl$_3$): 165.07, 158.92, 157.64, 154.78, 152.86, 152.39, 142.54, 138.36, 137.66, 137.33, 136.76, 136.71, 136.47, 133.38, 128.59, 128.53, 128.48, 128.43, 128.39, 128.25, 128.15, 128.08, 128.02, 127.98, 127.94, 127.90, 127.81, 127.75, 127.62, 127.50, 127.48, 127.21, 124.92, 109.06, 106.23, 101.29, 94.26, 93.78, 78.41, 75.10, 75.05, 71.22, 71.13, 70.09, 69.90, 69.80, 24.00.

To a solution of the fully benzyl protected gallate ester (100 mg, 84.8 μmol) obtained above in MeOH/THF (10/10 mL) was added Pd(OH)$_2$ (105 mg, 20% on carbon). The mixture was stirred at room temperature under H$_2$ and monitored by TLC. When the starting material was consumed (in about 4 hours), the mixture was filtered through cotton to remove the catalyst, and eluted with acetone (5.0 mL). The combined eluate was concentrated by rotary evaporator and vacuum drying to give the crude product which was purified by silica gel chromatography (EtOAc/CH$_2$Cl$_2$=2.5/1) to afford the pure (+)-GCG, 28.6 mg (74%) as a white solid. [a]$_D$=11.78 (c 0.78, THF); NMR (300 MHz, acetone-d/D$_2$O=2/1): 6.94 (s, 2H), 6.44 (s, 2H), 5.98 (d, J=2.5, 1H), 5.88 (d, J=2.5, 1H), 5.23 (q, J=6.6, 1H), 4.93 (d, J=6.6, 1H), 3.00 (dd, J=16.5, 5.2, 1H), 2.61 (dd, J=16.5, 6.6, 1H); $^{13}$C NMR (75 MHz, CDCl$_3$): 166.25, 156.73, 156.33, 155.24, 145.66, 145.22, 138.69, 132.97, 129.64, 120.34, 109.47, 106.07, 98.70, 95.87, 94.81, 78.30, 70.27, 24.25. The compound had identical NMR spectra as the commercially available natural (−)-GCG (Sigma, [a]$_D$=−12.44 (c 0.8, THF).

C. Synthesis of cis-(±)-5,7-Bis-benzyloxy-2-(3,4,5-tris-benzyloxyphenyl)-chroman-3-yl-amine ((±)-2) and the enantiomers (+)-2 and (−)-2

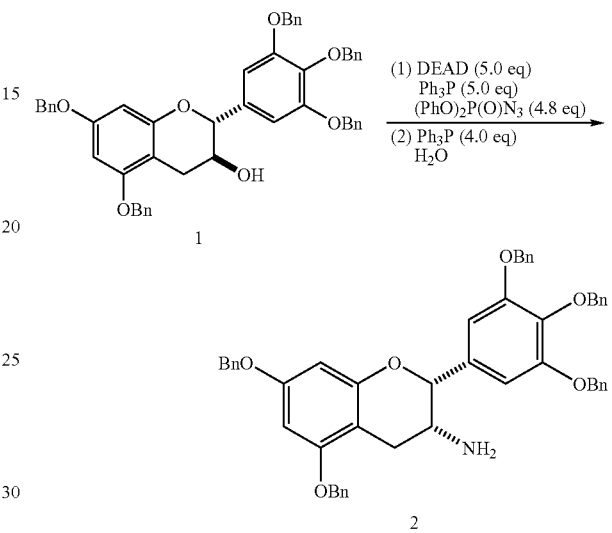

To a solution of (±)-trans-5,7-bis-benzyloxy-2-[3,4,5-tris (benzyloxy)phenyl]chroman-3-ol ((±)-1) (152.6 mg, 0.2 mmol) in THF (8.0 mL) was added triphenylphosphine (262.3 mg, 1.0 mmol), diethylazodicarboxylate (174.2 mg, 1.0 mmol) and diphenylphosphoryl azide (269.7 mg, 0.98 mmol) at room temperature. The solution was stirred at room temperature for 2 hours. EtOAc (20 mL) and H$_2$O (10 mL) were added and stirred for an additional 10 minutes. The layers were separated and the aqueous layer was extracted with EtOAc (4×50 mL). The combined organic phase was washed with brine (15 mL) and dried over anhydrous Na$_2$SO$_4$. The solution was concentrated by rotary evaporator and vacuum drying to give the crude product which was purified by silica gel chromatography (C$_6$H$_6$/EtOAc=100/1) to afford the mixture of desired product and the elimination by-product (ratio is about 1/1). This mixture was dissolved in THF (8.0 mL), after which triphenylphosphine (85 mg) and H$_2$O (65 mg) were added. The solution was refluxed overnight followed by addition of H$_2$O (180 mg) and then refluxed for 3 hours. The solution was concentrated by rotary evaporator and vacuum drying to give the residue which was purified by silica gel chromatography (C$_6$H$_6$/EtOAc=5/1) to afford pure product 42 mg (28%) of (±)-2 as a white solid. $^1$H NMR: (300 MHz, CDCl$_3$), 7.36 (m, 25H), 6.74 (s, 2H), 6.29 (s, 2H), 5.16 (s, 4H), 5.09 (s, 2H), 5.04 (s, 4H), 4.95 (s, 1H), 3.34 (m, 1H), 2.99 (dd, J=16.8, 5.2, 1H), 2.86 (dd, J=16.8, 1.9, 1H), 1.06 (s, br, 2H). $^{13}$C NMR: (75.5 MHz, CDCl$_3$), 158.47, 158.17, 154.86, 152.61, 137.79, 137.65, 136.85, 136.83, 136.74, 134.47, 128.46, 128.44, 128.37, 128.34, 128.19, 128.02, 127.86, 127.76, 127.72, 127.68, 127.41, 127.39, 127.04, 105.72, 101.44, 94.50, 93.83, 78.93, 75.16, 71.24, 70.08, 69.86, 48.27, 28.32. By employing the same procedure as described above, and starting from the appropriate enantiomer of 1, (−)-[2R,3]-5,7-bis-benzyloxy-2-(3,4,5-tris-benzyloxyphenyl)chroman-3-yl-amine ((−)-2), [α]$_D$=−14.6 (c=3.0, CHCl$_3$) and (+)-[2S,3S]-5,7-bis-benzyloxy-2-(3,4,5-tris-benzyloxyphenyl)chroman-3-yl-amine ((+)-2), [α]$_D$=16.8 (c=3.5, CHCl$_3$) were prepared with identical NMR spectra as (±)-2.

D. Synthesis of cis-(±)-3,4,5-Tris-benzyloxy-N-[5,7-bis-benzyloxy-2-(3,4,5-tris-benzyloxyphenyl)-chroman-3-yl]-benzamide ((±)-4) and the enantiomers (+)-4 and (−)-4

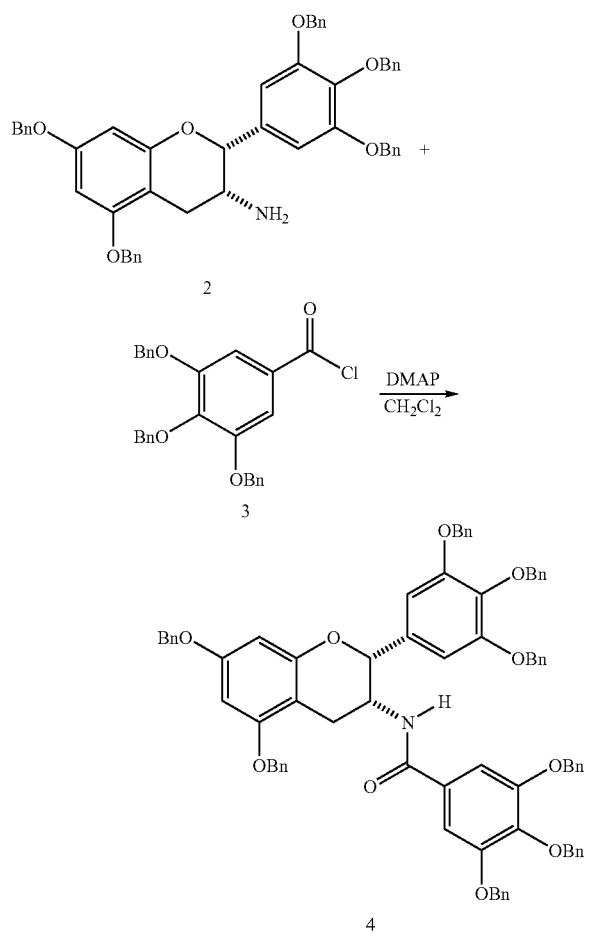

To a solution of (±)-2 (50 mg, 65.6 mmol) in CH$_2$Cl$_2$ (6.0 mL) was added DMAP (20 mg, 164 mmol). The solution was cooled to 0° C., and tris(benzyloxy)benzoic acid chloride (45 mg, 98.4 mmol) was added. The mixture was stirred at 0° C. for 2 hours, allowed to warm to room temperature, and was stirred overnight. Saturated NaHCO$_3$ aqueous solution (10 mL) was then added and stirred for 1 hour, layers were separated, and the aqueous layer was extracted with EtOAc (5×20 mL). The combined organic phase was washed with brine (15 mL) and dried over anhydrous Na$_2$SO$_4$. The solution was concentrated by rotary evaporator and vacuum drying to give the crude product which was purified by silica gel chromatography (C$_6$H$_6$/EtOAc=50/1) to afford the pure product 62.4 mg (81%) of (±)-4 as a white solid. $^1$H NMR: (400 MHz, CDCl$_3$), 7.33 (m, 40H), 6.87 (s, 2H), 6.80 (s, 2H), 6.36 (m, 2H), 6.31 (d, J=8.8, 1H), 5.06 (m, 18H), 3.11 (dd, J=17.3, 5.2, 1H), 3.03 (dd, J=17.3, 2.8, 1H). $^{13}$C NMR: (100.6 MHz, CDCl$_3$), 166.54, 158.63, 158.01, 154.90, 152.78, 152.42, 141.13, 138.11, 137.48, 137.17, 136.63, 136.52, 136.49, 136.29, 133.20, 129.74, 128.50, 128.42, 128.32, 128.29, 128.01, 127.96, 127.82, 127.76, 127.72, 127.62, 127.49, 127.39, 127.00, 106.76, 105.82, 101.75, 94.73, 94.27, 77.49, 75.15, 75.09, 71.42, 71.34, 70.18, 69.93, 45.99, 26.82. By employing the same procedure as described above, and starting from the appropriate enantiomer of 2, (−)-[2R,3R]-3,4,5-tris-benzyloxy-N-[5,7-bis-benzyloxy-2-(3,4,5-tris-benzyloxyphenyl)-chroman-3-yl]-benzamide ((−)-4), [α]$_D$=−14.5 (c=4.7, CHCl$_3$) and (+)-[2S,3S]-3,4,5-tris-benzyloxy-N-[5,7-bis-benzyloxy-2-(3,4,5-tris-benzyloxyphenyl)-chroman-3-yl]-benzamide ((+)-4), [α]$_D$=10.9 (c=4.5, CHCl$_3$) were prepared with identical NMR spectra as the (±)-4.

E. Synthesis of cis-(±)—N-[5,7-Dihydroxy-2-(3,4,5-trihydroxyphenyl)-chroman-3-yl]-3,4,5-trihydroxybenzamide ((±)-5 and the enantiomers (+)-5 and (−)-5

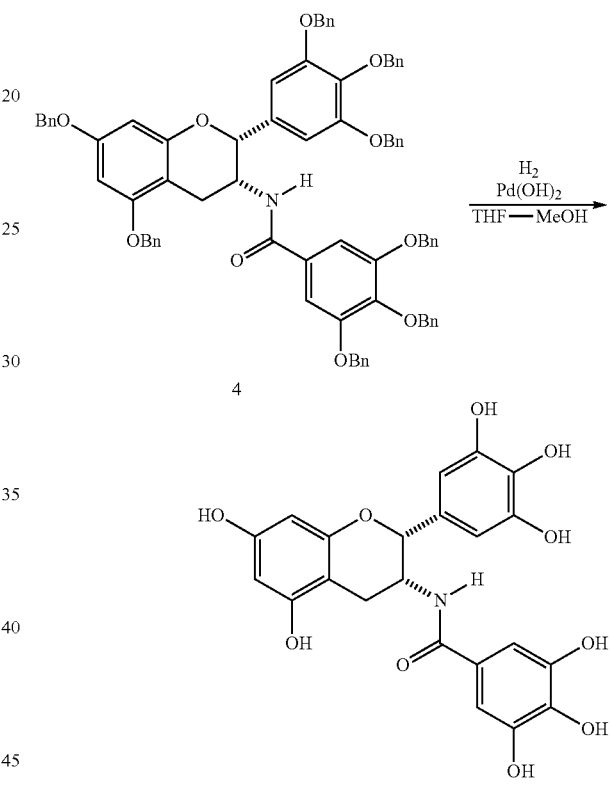

To a solution of (±)-4 (45.5 mg, 38.6 µmol) in THF/MeOH (4.5/4.5 mL) was added Pd(OH)$_2$ [20 wt. % Pd (dry basis) on carbon] (50 mg). The mixture was stirred at room temperature under H$_2$ and monitored by TLC. Two hours later, the starting material was consumed according to TLC analysis. The Pd catalyst was removed by filtering through cotton, and eluted with acetone (4.0 mL). The combined elute was concentrated by rotary evaporator and vacuum drying to give the crude product which was purified by reverse phase column chromatography (MeOH/H$_2$O=4/6) to afford the pure product 14.5 mg (82%) of (±)-5 as a pale yellow solid. $^1$H NMR: (400 MHz, acetone-d/D$_2$O=2/1), 7.00 (d, J=8.0, 1H), 6.68 (s, 2H), 6.54 (s, 2H), 5.98 (d, J=2.2, 1H), 5.92 (d, J=2.2, 1H), 5.01 (d, J=1.4, 1H), 4.53 (m, 1H), 2.87 (dd, J=16.8, 5.2, 1H), 2.75 (dd, J=16.8, 3.0, 1H). $^{13}$C NMR: (100.6 MHz, acetone-d/D$_2$O=2/1), 168.13, 156.58, 156.42, 155.60, 145.50, 145.12, 136.68, 132.32, 129.99, 124.82, 107.03, 105.43, 99.29, 96.18, 95.27, 77.26, 47.57, 26.32. By employing the same procedure as described above, and starting from the appropriate enantiomer of 4, (−)-[2R,3R]-N-[5,7-Dihydroxy-2-(3,4,5-trihydroxyphenyl)-chroman-3-yl]-3,4,5-trihydroxybenzamide ((−)-5), $[\alpha]_D=-112$ (c=0.95, acetone/$H_2O$=2/1) and (+)-[2S, 3S]-N-[5,7-Dihydroxy-2-(3,4,5-trihydroxyphenyl)-chroman-3-yl]-3,4,5-trihydroxybenzamide ((+)-5), $[\alpha]_D=101$ (c=0.67, acetone/$H_2O$=2/1) were prepared with identical NMR spectra as the (±)-5.

Example 8

(−)-EGCG Kinetics

A kinetics experiment showing the decrease in chymotrypsin-like activity over time was conducted. (−)-EGCG at 1 µM potently inhibited the chymotrypsin-like activity of a purified eukaryotic (rabbit) 20S proteasome in a time-dependent manner: 35% at 5 min, 62% at 30 min, and 70-80% after 1 to 3 hours (FIG. 7), which is characteristic for a mechanism-based inhibitor. This result further demonstrates that the mode of (−)-EGCG action is irreversible inhibition.

Figure 7:
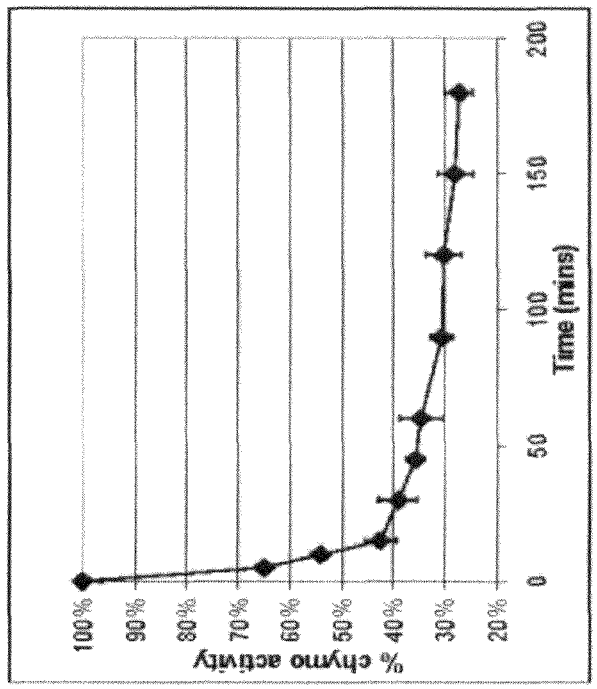
FIG. 7 shows a graph for the kinetics of (−)-EGCG-mediated proteasome inhibition as discussed in Example 4.

(−)-EGCG at 1 µM was incubated with eukaryotic 20S proteasome (0.02 µg) and suc-LLVY-AMC (20 µM) for the times indicated in FIG. 7. The chymotrypsin activity was measured and graphed in FIG. 7. Values are means from 4 independent experiments, and error bars represent standard deviations.

Example 9

Proteasome Inhibition by EGCG and its Analogs

Figure 2A:
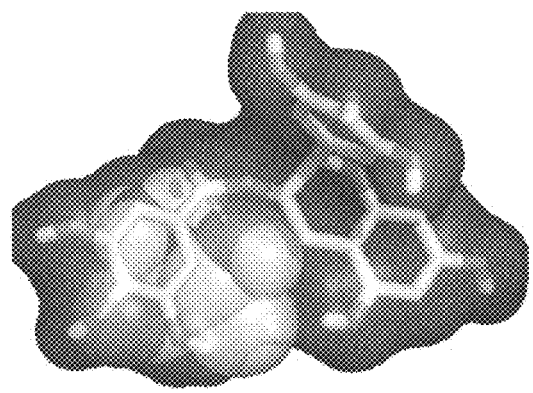
FIG. 2A shows a view of the docking solution of (−)-EGCG and 20S proteasome. The dotted yellow line represents the distance from the hydroxyl of Thr 1 to the carbonyl carbon of (−)-EGCG.

There are two aspects of proteasome inhibition by (−)-EGCG. First, it was demonstrated that (−)-EGCG irreversibly inhibits the chymotrypsin-like activity of the proteasome in a time-dependant manner (FIGS. 6 and 7), so it is plausible that a nucleophilic attack of the ester bond carbon of (−)-EGCG occurs. Secondly, in order for the above event to occur, (−)-EGCG must bind to the active site in the appropriate orientation and conformation that allows for attack of the carbonyl carbon of (−)-EGCG to take place (FIG. 2A).

Figure 2B:
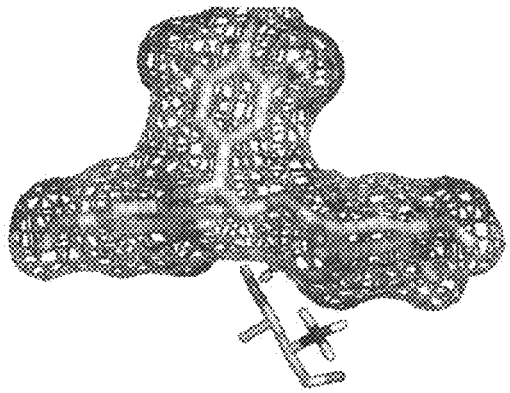
FIG. 2B shows an overview of (−)-EGCG binding mode to the $\beta_5$ subunit. The color code is: red, oxygen; blue, nitrogen; gray, carbon; and white, hydrogen.
Figure 2C:
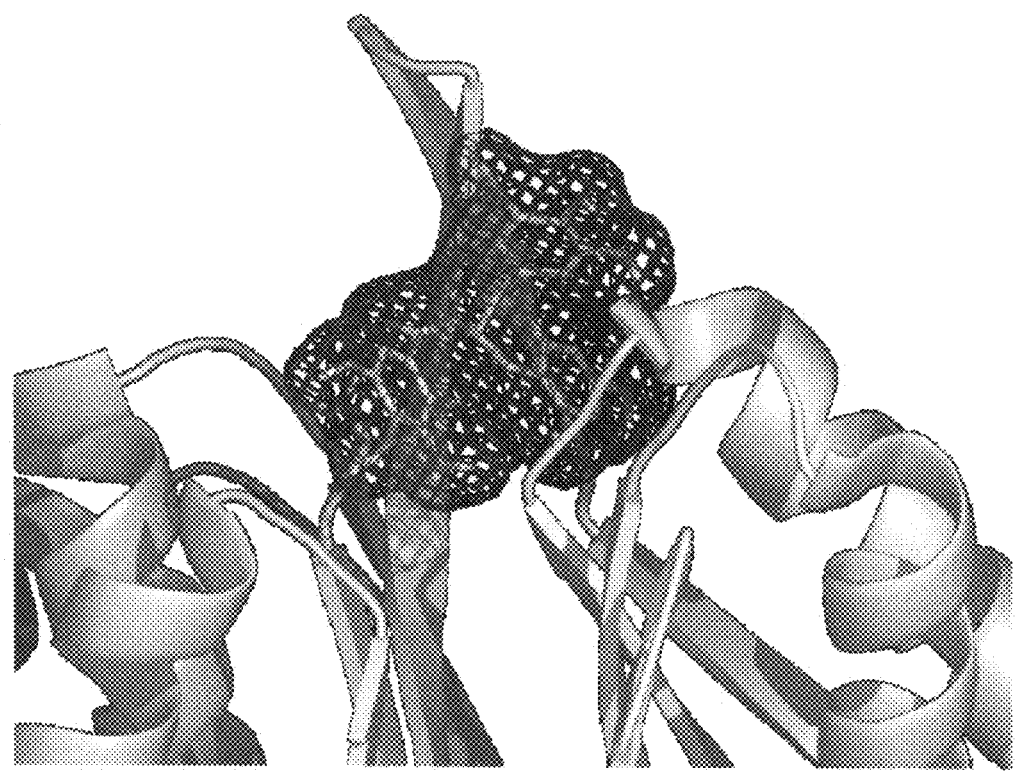
FIG. 2C shows (−)-EGCG as a slick model with a mesh surface, bound to the β5 binding cleft (ribbon representation).
Figure 2D:
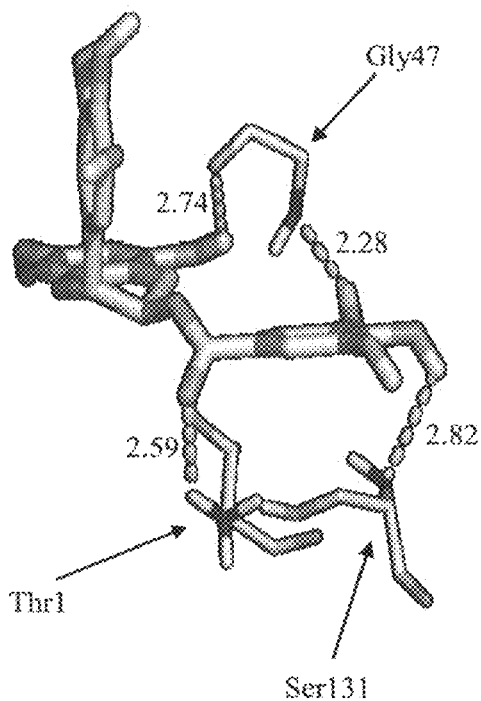
FIG. 2D shows eight potential hydrogen (H) bonds formed between (−)-EGCG and indicated amino acids, with the yellow dotted lines representing H-bonds and the numbers next to the lines representing f1-bond distances in Angstroms. The color code is red: oxygen; blue: nitrogen; gray: carbon; and white: hydrogen.
Figure 2E:
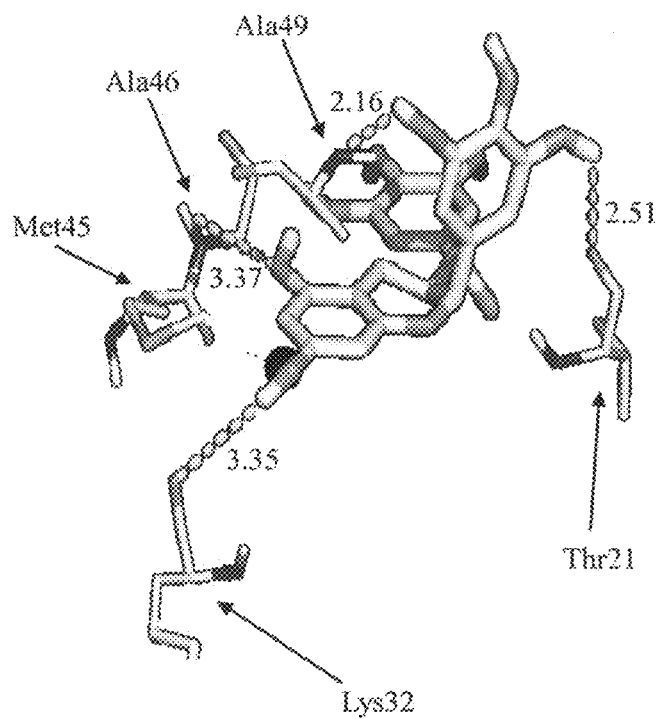
FIG. 2E also shows eight potential hydrogen (H) bonds formed between (−)-EGCG and indicated amino acids, with the yellow dotted lines representing H-bonds and the numbers next to the lines representing f1-bond distances in Angstroms. The color code is red: oxygen; blue: nitrogen; gray: carbon; and white: hydrogen.

(−)-EGCG can bind the proteasome's chymotrypsin active site in an orientation and conformation that is well suited for nucleophilic attack as described by the following model. First, eight H bonds can form between (−)-EGCG and the β5 subunit (FIGS. 2D and 2E). Second, favorable hydrophobic surface interactions exist (tyrosine-like mimic in S1 pocket) (FIGS. 2D and 2E). Third, there is a large potential van der Walls contact surface area (FIG. 2C). Fourth, the calculated free energy values are favorable for binding of (−)-EGCG to the proteasome (FIG. 3A). Fifth, it is likely that the scissile bond of (−)-EGCG is strained, suggesting lowering of the activation energy for the formation of the tetrahedral intermediate in the proposed acylation reaction (FIG. 4). Finally, it was observed that one of the two docked structures of lowest free energy for (−)-EGCG had its electrophilic carbonyl carbon 3.18 Å from the hydroxyl group of Thr 1 (FIGS. 2A and 2B). All these properties demonstrated by this reported docking model have supplied an attractive, empirically directed, analog supported model of proteasome inhibition by the green tea polyphenol (−)-EGCG.

Figure 15:
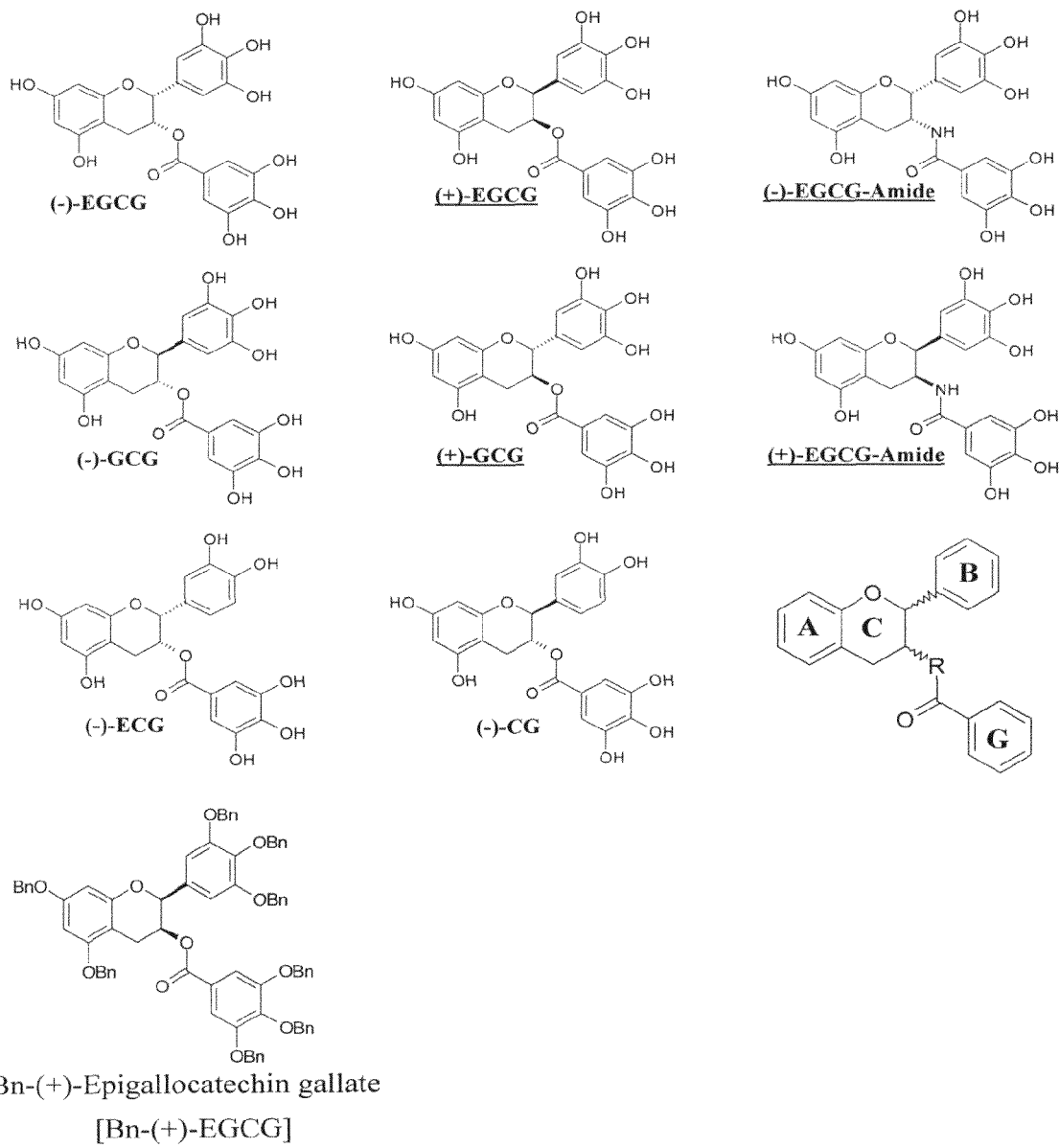
FIG. 15 shows structures of synthetic and natural greet tea polyphenols.

Novel analogs of naturally occurring tea polyphenols have been synthesized. Such analogs have been tested for their inhibitory potencies against the proteasome. Two analogs of (−)-EGCG were synthesized. The first analog, (+)-EGCG, was the enantiomer (mirror image) of the natural (−)-EGCG, having the 2R, 3R configuration instead of the natural 2S, 3S configuration. [FIG. 15, (−)-EGCG vs. (+)-EGCG]. The second analog, Bn-(+)-EGCG, was synthesized with all eight hydroxyls protected by benzyl groups. This should eliminate any hydrogen bonding created by the hydroxyls in (+)-EGCG while maintaining the integrity of the ester bond. In addition the enantiomer of the natural (−)-GCG was also synthesized, giving (+)-GCG with the 2R, 3S configuration [FIG. 15, (−)-GCG and (+)-GCG].

Figure 16A:
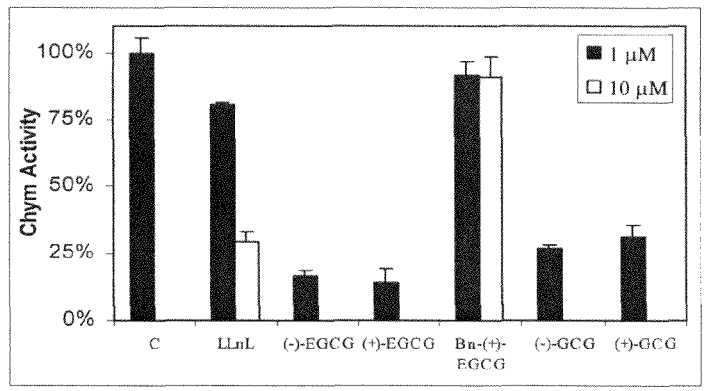
FIG. 16A shows a bar graph of the inhibition of proteasomal activity by synthetic and natural GTPs.
Figure 16B:
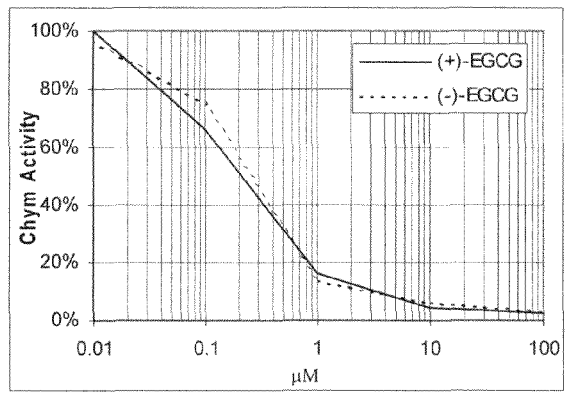
FIG. 16B shows a graph of the decrease in proteasomal activity as the concentration of (+)-EGCG and (−)-EGCG increases.
Figure 16C:
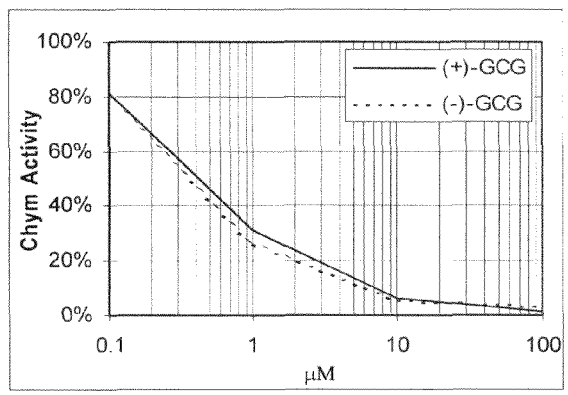
FIG. 16C shows a graph of the decrease in proteasomal activity as the concentration of (+)-GCG increases.

The ability of each purified synthetic GTP analog to inhibit the chymotrypsin-like activity of purified 20S proteasome, using the natural GTPs for comparison was determined. In this experiment, the synthetic (+)-EGCG at 1 µM inhibited 86% of the proteasomal activity, similar to that of its natural counterpart, (−)-EGCG (FIG. 16A). However, the benzyl-protected compound, Bn-(+)-EGCG, did not significantly inhibit the proteasome activity even at 10 µM concentrations (FIG. 16A), demonstrating the requirement of one or more hydroxyl groups for the proteasome-inhibitory activity of EGCG. The synthetic (+)-GCG was found to inhibit 70% of the proteasomal activity at 1 µM, similar to the natural (−)-GCG (FIG. 16A). Both forms of EGCG are more potent than the two GCG analogs (FIG. 16A). As a control in this experiment, a well-known tripeptidyl proteasome inhibitor LLnL at 1 and 10 µM inhibited 20 and 70% proteasomal activity, respectively (FIG. 16A).

To further determine the proteasome-inhibitory activities of the synthetic GTP analogs, multiple concentrations of each GTP was used in order to measure their one-half maximal inhibition values ($IC_{50}$s). An $IC_{50}$ of 210 nM was found for the synthetic (+)-EGCG, similar to the control (−)-EGCG (FIG. 2B). In addition, the (+)-GCG compound, similar to the natural (−)-GCG, produced an $IC_{50}$ value of 410 nM, nearly twice that of (+)-EGCG (FIGS. 2B and 2C). Dose-dependant inhibition of purified 20S proteasome by (+)-EGCG and (−)-EGCG (B), or (+)-GCG and (−)-GCG (C) is graphed on a log plot. All values are means of independent triplicate experiments. Error bars denote standard deviations (error bars were not included on B and C for clarity of presentation)

Figure 3B:
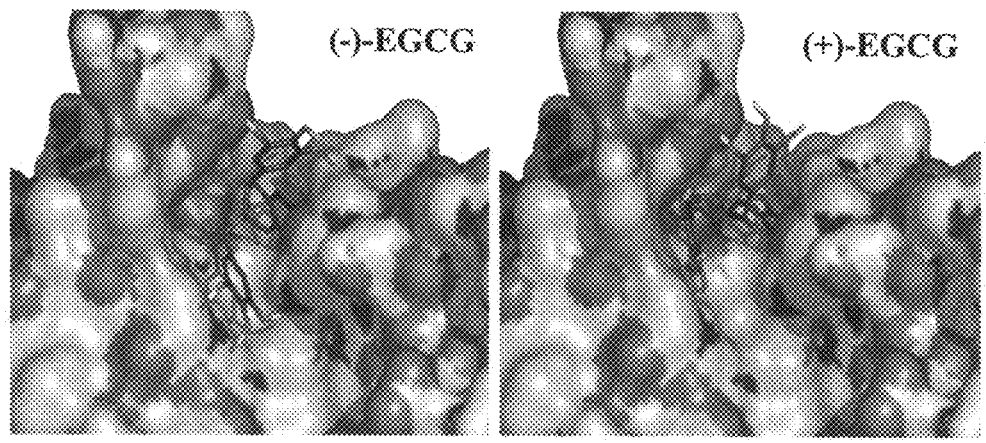
FIG. 3B shows the binding mode of (+)-EGCG.
Figure 1:
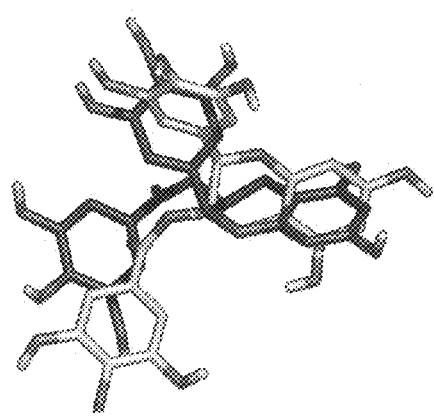
Figure 17A:
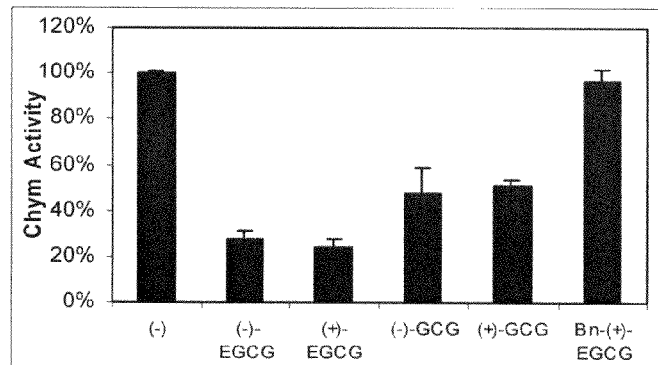
FIG. 17A shows a bar graph of chymotrypsin activity in the presence of natural and synthetic GTPs.
Figure 17B:
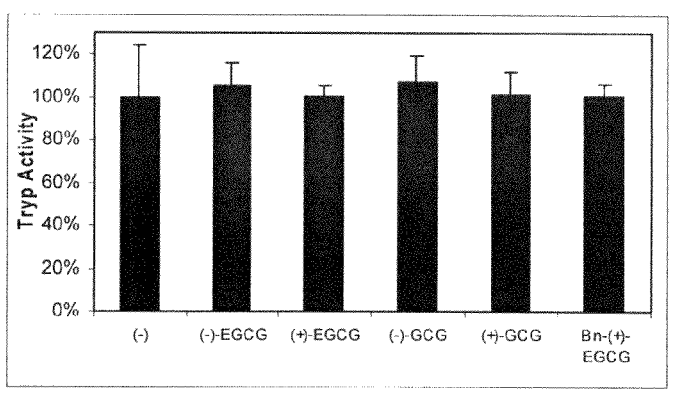
FIG. 17B shows a bar graph of trypsin activity in the presence of natural and synthetic GTPs.
Figure 17C:
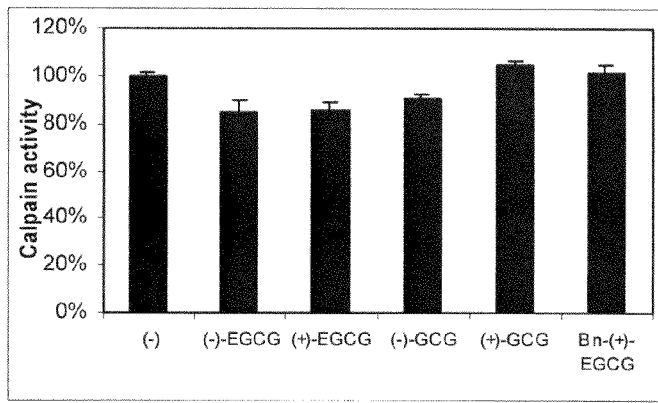
FIG. 17C shows a bar graph of calpain activity in the presence of natural and synthetic GTPs.

To determine the specificity of the synthetic GTP analogs, their effects were tested on the chymotrypsin-like and trypsin-like activities of the 26S proteasome in a Jurkat cell lysate. Similar to inhibition of the purified 20S proteasome, the synthetic (+)-EGCG at 10 µM inhibited 76% of the chymotrypsin-like activity of 26S proteasome in cell lysates (FIG. 17A). In contrast, the Bn-(+)-EGCG analog could not inhibit the proteasomal chymotrypsin activity at all (FIG. 3A). (+)-GCG at the same concentration inhibited ~50% of the chymotrypsin-like activity. The potencies of (+)-EGCG and (+)-GCG were similar to those of their natural partners, respectively (FIG. 17A). However, none of the synthetic or natural GTPs could significantly inhibit the proteasomal trypsin-like activity in the Jurkat cell extract (FIG. 3B). Furthermore, none of the synthetic or control natural compounds could inhibit more than 15% of activity of a purified calpain enzyme (FIG. 17C). These data strongly suggest that the synthetic GTPs with ester bonds selectively inhibit the chymotrypsin-like activity of the proteasome. Values are mean triplicates and error bars denote standard deviations.

Figure 18A:
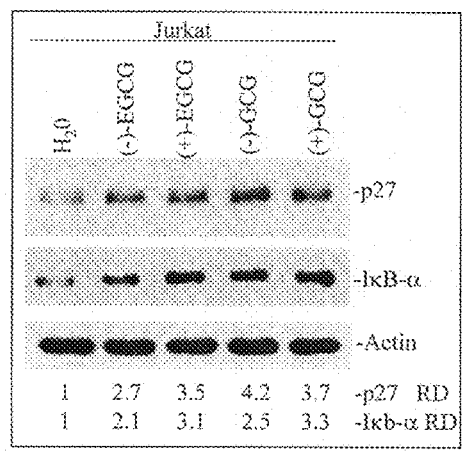
FIG. 18A shows the accumulation of p27 and IkB-a proteins in Jurkat cells.

A. Accumulation of Proteasome Target Proteins P27 and IκB-a and Induction of Tumor Cell $G_1$ Arrest by Synthetic GTPs Having discovered that the synthetic GTP analogs are potent and specific inhibitors of the proteasomal chymotrypsin-like activity in vitro (FIGS. 16A, 17A, 17B, and 17C), it was then determined whether the synthetic compounds could also be effective in inhibiting intact tumor cell proteasome activity. Because inhibition of the proteasome activity in tumor cells would result in increased levels of proteasome target proteins, levels of p27 and IκB-a proteins were measured by Western blot assay in Jurkat T cells treated with each GTP. After a 12 hour treatment, (+)-EGCG at 10 µM accumulated p27 and IκB-a levels by 3.5- and 3.1-fold, respectively (FIG. 18A). In comparison, the natural (−)-EGCG accumulated p27 and IκB-a, to a slightly lesser extent, by 2.7- and 2.1-fold, respectively (FIG. 18A). In addition, synthetic (+)-GCG increased p27 and IκB-a levels by 3.7- and 3.3-fold, respectively, similar to the results from (−)-GCG treatment (FIG. 18A).

Figure 18B:
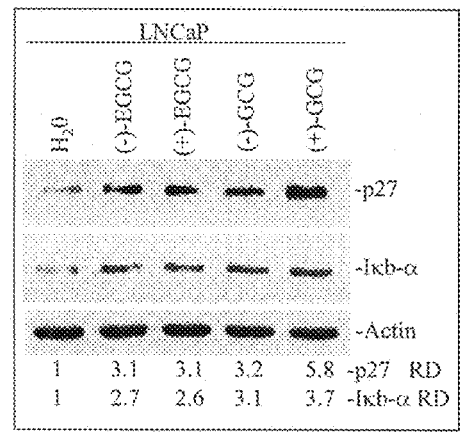
FIG. 18B shows the accumulation of p27 and IkB-a proteins in LNCaP cells.

The above experiment was also performed in prostate cancer LNCaP cells. The synthetic (+)-EGCG increased the levels of p27 and IκB-a by 3.1 and 2.6-fold, respectively, comparable to the effects of (−)-EGCG (FIG. 18B). A 5.8- and 3.7-fold increase in p27 and IκB-α levels, respectively, was observed after treatment with (+)-GCG (FIG. 18B). The control compound (−)-GCG did not accumulate as much p27 protein as the synthetic compound did, although both compounds accumulated similar levels of IκB-a (FIG. 18B).

Molecular masses of IκB-a and actin are 40 and 43 kDa, respectively. Relative Density (RD) values are normalized ratios of the intensities of p27 and IkB-a band to the corresponding actin band. Data is representative of at least three independent experiments It has been shown that overexpression of p27 and IκB-a results in $G_1$ arrest. If increased levels of these proteasome target proteins by synthetic GTPs are functional, it would be expected to see growth arrest of tumor cells in $G_1$ phase. To test this hypothesis, asynchronous prostate LNCaP cells were treated with 10 µM of synthetic (+)-EGCG or (+)-GCG, along with each respective natural GTP as control, for 24 hours. Cells were then harvested, and analyzed by cell cycle analysis by flow cytometry. The amount of $G_1$, S and $G_2$/M cell populations was demonstrated by DNA histogram. Growth arrest was determined by the increase in the percentage of the $G_1$ population.

Figure 19:
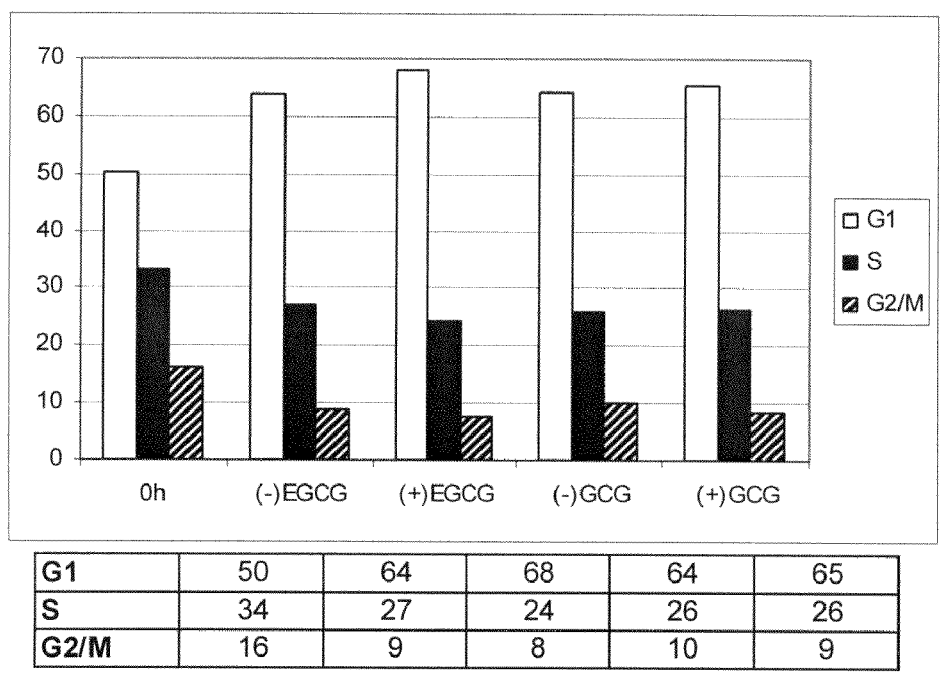
FIG. 19 shows that synthetic GTPs induce G1 arrest in prostate cancer LNCaP cells.

It was observed that treatment with each of the GTPs significantly increase the $G_1$ population, accompanied by a reduction in S and $G_2$/M phase cell populations. Specifically, the synthetic (+)-EGCG increased the $G_1$ population by 18%, while (−)-EGCG, (+)-GCG and (−)-GCG all induced ~14% $G_1$ arrest (FIG. 19, C for control). Therefore, the synthetic GTPs have the ability to inhibit prostate tumor cell growth, with potency either similar to, or even greater than, that of the natural compounds. Data is representative of at least three independent experiments.

B. Accumulation of the Pro-Apoptotic Bax Protein and Activation of Tumor Cell Apoptotic Program by Synthetic GTPs The pro-apoptotic protein Bax is another target protein of the proteasome. To investigate whether synthetic tea polyphenols have the ability to induce Bax-associated cancer cell apoptosis, two human prostate cancer cell lines, LNCaP and DU145, were used. LNCaP cells express much higher levels of Bax protein than DU145 cells. The comparison between these two cell lines provides an excellent model for studying the role of Bax in the process of GTP-mediated proteasome inhibition and apoptosis induction.

Figures 20A, 20B:
FIG. 20A shows Bax-associated cancer cell apoptosis in cells of two human prostate cancer cell lines, LNCaP and DU145. High Bax protein (21 kDa) levels in LNCaP cells, and very low Bax expression in DU145 cells were observed.
FIG. 20B shows results of a Western blot using antibodies specific to Bax and actin, where LNCaP or DU-145 cells were previously treated for 24 hours with either $H_2O$ (C, for control) or 10 μM (−)-EGCG or (+)-EGCG.
Figure 20C:
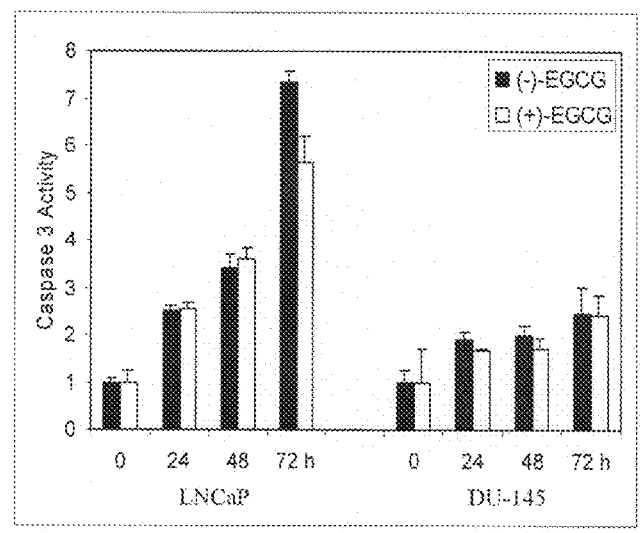
FIG. 20C shows a bar graph of caspase 3 activity in LNCaP cells and DU145 cells determined by cell-free caspase-3 activity assay following treatment with (−)-EGCG and (+)-EGCG for the indicted hours.
Figure 20D:
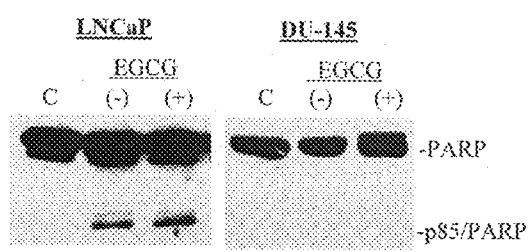
FIG. 20D shows results of a Western blot using PARP-specific antibody, where LNCaP or DU-145 cells were previously treated for 24 hours with either $H_2O$(C, for control) or 10 μM (−)-EGCG or (+)-EGCG. (+)-EGCG, as well as (−)-EGCG, induced the apoptosis-specific PARP cleavage only in LNCaP, but not DU145 cells.

Exponentially growing LNCaP and DU-145 prostate cells were harvested and the levels of Bax protein was detected by Western blot analysis (FIG. 20A). A high-molecular-weight band, recognized by the anti-Bax antibody, is indicated by an arrowhead. Although its nature remains unknown, this high-molecular-weight band can be used as a loading control. LNCaP or DU-145 cells were treated for 24 hours with either $H_2O$(C, for control) or 10 µM (−)-EGCG or (+)-EGCG (FIG. 20B). Cells were then harvested and Western-blotted with specific antibodies to Bax, actin (FIG. 20B) or PARP (FIG. 20D). Data are representative of at least three independent experiments.

High Bax protein (21 kDa) levels in LNCaP cells, and very low Bax expression in DU145 cells were also observed (FIG. 20A). Treatment of LNCaP cells for 24 hours with synthetic (+)-EGCG at 10 µM significantly increased Bax protein levels, similar to the effect of the natural (−)-EGCG (FIG. 20B). In contrast, neither (+)-EGCG nor (−)-EGCG was able to increase the levels of Bax protein in DU145 cells (FIG. 20B).

To examine whether (+)-EGCG could induce apoptosis only in LNCaP, but not DU-145, cells, both cell lines were treated with 10 µM (+)-EGCG for 0, 24, 48 or 72 hours, followed by performance of cell-free caspase-3 activity assay. Cells were harvested at each sequential time-point and activity was determined by incubating whole cell extracts with caspase-3 substrate and measuring free AMCs (FIG. 20C). All the time-points were normalized to 0 hours. (+)-EGCG activated caspase-3 in LNCaP cells in a time-dependent manner: by 2.5-, 3.5- and 6-fold at 24, 48 and 72 hours, respectively (FIG. 20C). In contrast, little caspase-3 activity was detected in (+)-EGCG-treated in DU145 cells: only-2-fold induction at 72 hours (FIG. 20C). In the same experiment, (−)-EGCG at 10 µM was used as a control. It was found that the potency of (+)-EGCG to activate caspase-3 was comparable to that of (−)-EGCG in both LNCaP and DU145 cells (FIG. 20C). Consistent with that finding, (+)-EGCG, as well as (−)-EGCG, induced the apoptosis-specific PARP cleavage only in LNCaP, but not DU145 cells (FIG. 20D). Therefore, the abilities of (+)-EGCG to activate apoptotic program in these prostate cancer cell lines are correlated well to their abilities to accumulate Bax protein levels to a critical high threshold (compare FIGS. 20C and 20D vs. 20B). Values are means of triplicate independent experiments and error bars denote standard deviations. These data suggest that EGCG accumulated Bax protein plays an essential role in activating caspases and inducing apoptosis in human prostate cancer cells.

The physiological concentration of a single GTP (such as EGCG) has been observed to be in the single digit µM to high nanomolar ranges. Therefore, if a GTP of interest is to function physiologically, the mechanism of action must therefore occur at concentrations similar to those found for GTPs in serum.

Synthesis of GTP analogs should also prove beneficial for determining which mechanisms are responsible for the observed anti-cancer effects. For example, it is possible that the kinase-inhibitory activity of EGCG could be removed in some EGCG analogs while retaining the proteasome-inhibitory activities, and vice-versa. These synthetic GTP analogs could therefore help to solve the problem of distinguishing the important mechanistic properties of tea polyphenols.

Synthetic GTPs are active and comparable to their natural counterparts in biological assays. The proteasome-inhibitory potency of the synthetic (+)-EGCG was found to be similar to, and sometimes higher than, that of the natural stereoisomer (−)-EGCG (FIGS. 2-7). A similar characteristic was also found for the (+)-GCG compound and its control (−)-GCG. However, the benzyl-protected compound, Bn-(+)-EGCG, which has no available hydroxyls for hydrogen binding, can not inhibit the proteasome despite the presence of the ester-bond that is susceptible to a nucleophilic attack by the proteasome's N-terminal threonine. This suggests that hydrogen bonding to some or all of EGCG's eight OH groups are important in binding to the proteasome active site for inhibition. However, introduction of eight such benzyl groups would also no doubt add a lot of mass to EGCG as well as cause other steric difficulties during proteasomal binding in addition to the elimination of hydrogen bonding potentials.

The aforementioned experiments demonstrate that the synthetic enantiomers of these two GTPs, (+)-EGCG and (+)-GCG, at least did not loose any, and even may have gained some potency in regards to proteasome inhibition. FIGS. 17A, 17B, and 17C also demonstrate that the specificity profile is also the same in regards to three different protease activities: chymotrypsin-like, trypsin-like, and calpain. This at least suggests that the synthetic stereoisomers are inhibiting via a similar mechanism as the natural occurring compounds. Normally, most biological processes show chiral discrimination, where enantiomers display different biological activities. While it is too early to speculate on the reason for the lack of chiral discrimination in the present case, an argument can be made that the presence of the two trihydroxyphenyl rings in EGCG (or GCG) may have rendered the molecule pseudo-symmetric in terms of its binding to the active site of proteasome.

It has been suggested that under in vivo conditions, GTPs, specifically (−)-EGCG, are unstable and can be degraded or altered, quickly making them unavailable for inhibition of enzymatic activities. It was then thought that synthetic GTPs might have identical potencies as natural ones, but with increased stability. To test this idea synthetic and natural GTP compounds were used in both suspension (Jurkat) and solid tumor (LNCaP) cell lines to determine their ability to accumulate proteins that are degraded by the proteasome. In Jurkat cells this hypothesis seemed at least partially fulfilled because there was nearly a 30% increase in p27 levels and a 47% increase in IκB-a levels in cells treated with (+)-EGCG, as compared to (−)-EGCG (FIG. 18A). However, the accumulation of p27 and IκB-a levels in LNCaP cells was nearly identical for both (+)-EGCG as well as (−)-EGCG (FIG. 18B). The (+)-GCG compound also increased the levels of both proteins to higher levels in both cell lines as compared to the (−)-GCG compound, except p27 in Jurkat cells (FIGS. 18A and 18B). Though these differences are marginal it at least suggests the possibility that synthetic enantiomers may have better effects in animal models and clinical trials than do their natural counterparts, possibly due to an increase in drug stability in vivo.

In agreement with p27 and IκB-a accumulation in the in vivo experiments, cell cycle arrest was also observed after LNCaP cells were treated with these GTPs. Again, (+)-EGCG was found to be the most potent compound and induced an 18% $G_1$ arrest, compared to the positive control (−)-EGCG which induced 14% $G_1$ arrest, an approximately 30% increase just by changing the stereochemistry of the natural compound (FIG. 19). Again, this could suggest an increased stability of the synthetic compound might be responsible for increased ability to induce growth arrest.

To better determine whether these synthetic compounds induce Bax-dependent apoptosis, a pair of prostate cancer cell lines with either high or low Bax protein expression were used. It has been demonstrated that proteasome inhibitors can induce tumor cell death via accumulation of the pro-apoptotic Bcl-2 family member Bax. GTPs have been shown to induce apoptosis, so it was hypothesized that the synthetic EGCG analog should be able to accumulate levels of Bax and induce apoptosis in LNCaP cells which contain high basal levels of Bax, but should not induce apoptosis in DU-145 cells which express low Bax protein. Indeed, when these two prostate cancer cell lines were treated with either (+)-EGCG or natural (−)-EGCG, apoptosis was induced by both compounds in LNCaP cells but not in DU-145 cells, as judged by caspase-3 activation and PARP cleavage (FIG. 20A). This suggests that the synthetic EGCG analog can induce apoptosis in a Bax-dependant manner, supporting the conclusion that apoptosis would have been initiated via inhibition of proteasome-mediated Bax degradation.

The desired effect of any anti-tumor compound including cancer-preventative agents is to inhibit tumor growth and formation in situ. An assay developed to semi-mimic cellular growth in tissue is the colony forming soft agar assay. The synthetic GTPs that can inhibit the proteasome activity and cell cycle progression as well as induce cell death should be able to inhibit colony formation in a soft agar assay. Indeed, when LNCaP tumor cells were cultured in the presence of synthetic GTPs, an almost complete inhibition of colony formation was observed, as compared to the solvent control and the inactive Bn-(+)-EGCG (FIG. 21A).

Example 10

(−)-EGCG and Analogs Docking Studies (−)-EGCG's susceptibility to a nucleophilic attack is demonstrated in the HPLC results that showed that the proteasome could attack and degrade (−)-EGCG. Kinetic analysis and X-ray diffraction studies using the specific proteasome inhibitor lactacystin have demonstrated that the ester bond of this inhibitor covalently modifies the N-terminal threonine of the β5 subunit, which is critical for proteasome inhibition. Since (−)-EGCG contains an ester bond (FIG. 1) and inhibits the proteasome irreversibly in a time-dependent manner (FIGS. 6 and 7), it is probable that a lactacystin-like reaction occurs with (−)-EGCG.

A. Automated Docking of (−)-EGCG to the β5 Subunit of 20S Proteasome

To build a model for how (−)-EGCG binds to the proteasome, which will allow for nucleophilic attack, automated docking studies were performed. Knowledge of the enzyme kinetics discussed above can help direct docking solutions that would allow covalent modification and inhibition of the proteasome.

Before acylation of Thr 1's hydroxyl by (−)-EGCG can occur, (−)-EGCG must bind to the β5-active site in a conformation that would allow a reaction to occur between the two atoms involved. Binding of (−)-EGCG in an appropriate orientation and conformation is therefore necessary for ester bond scission because the presence of an ester bond alone is insufficient to inhibit the proteasome. This is demonstrated by benzyl protected-EGCG, which has an ester-bond, but cannot inhibit the proteasome. In addition, several small molecular weight molecules that contain ester bonds, including methyl acetate, benzyl hydroxybenzoate, and methyl gallate, cannot inhibit the proteasome.

Docking modes were therefore chosen based on the following two pre-defined criteria. First, the distance between the carbonyl carbon of (−)-EGCG and the hydroxyl of Thr 1 must be between 3-4 Å. Secondly, the ring system must be located within the S1 pocket. Based on these two criteria, the lowest docked free energy (negative G) was chosen for such a bound conformation. After docking (−)-EGCG to the β5 chymotrypsin active site, the ester bond of (−)-EGCG in one of the two lowest free energy docked structures could be easily found oriented directly over the Thr 1 side-chain and the ester bond-carbon was located 3.18 Å away from the hydroxyl of Thr 1 (FIGS. 2A and 2B). Such an orientation/conformation of the inhibitor is well suited for nucleophilic attack and is structurally achievable, which satisfies the first pre-defined criterion.

In addition, the fairly hydrophobic AC rings of (−)-EGCG (see FIG. 1) were oriented in the S1 pocket of the β5 subunit, the B ring projected up into solvent, bridging the two walls of the binding cleft, and the gallate (G) group sat above Ser 131 (FIGS. 2A and 3A). (−)-EGCG filled the majority of the binding cleft which was seen by drawing a water accessible mesh surface around (−)-EGCG when docked into the binding site as depicted by a ribbon structure of the β5 subunit (FIGS. 2B and 2C). The occupancy of the S1 pocket satisfied the second criterion, and the docking mode chosen possessed a free energy of −10.52 kcal/mol. This resultant model supports the hypothesis that (−)-EGCG first binds to the β5 active site and then is attacked by the N-terminal threonine, rendering the proteasome inactive by acylation.

There are eight polar hydrogens and one carbonyl-oxygen on (−)-EGCG that are available for H-bonding (see FIG. 1). It appears that all but two of these sites are actively participating in H-bonding. It should be noted that a relatively loose criterion was employed to establish the presence of a hydrogen bond because this structure is not energy minimized nor have its hydrogen bond distances been optimized.

The carbonyl oxygen of (−)-EGCG H-bonds with the side chain hydrogen on Thr 1 of the β5 subunit, with a calculated hydrogen bond distance 2.59 Å (FIG. 2D). In addition, two hydroxyls on the G ring H-bond with the backbone nitrogen atoms of Ser 131 and Gly 47 (2.82 and 2.28 Å, respectively; FIG. 2D). Furthermore, the A ring-hydroxyl of (−)-EGCG, which is further from the C ring, appears to be H-bonding with the backbone carbonyl of Gly 47 (2.74 Å; FIG. 2D) and the backbone nitrogen of Ala 46 (3.37 Å; FIG. 2E). The other A ring-hydroxyl H-bonds with the carbonyl oxygen of Lys 32 (3.35 Å; FIG. 2E). Finally, two of the EGCG B ring hydroxyls, which bridge the binding cleft (see FIGS. 2A and 3A), are H-bonded to the side chain of Thr 21 and the backbone nitrogen of Ala 49 (2.51 and 2.16 Å, respectively; FIG. 2E). This analysis has identified eight H-bonds, which seem important for (−)-EGCG binding to the proteasome β5 subunit. Consistent with this analysis, the fully benzyl protected-EGCG without free OH groups, which should not form H-bonds, fails to inhibit the proteasome and could not be found docked in an orientation/conformation that met criteria 1 and 2.

Figure 2F:
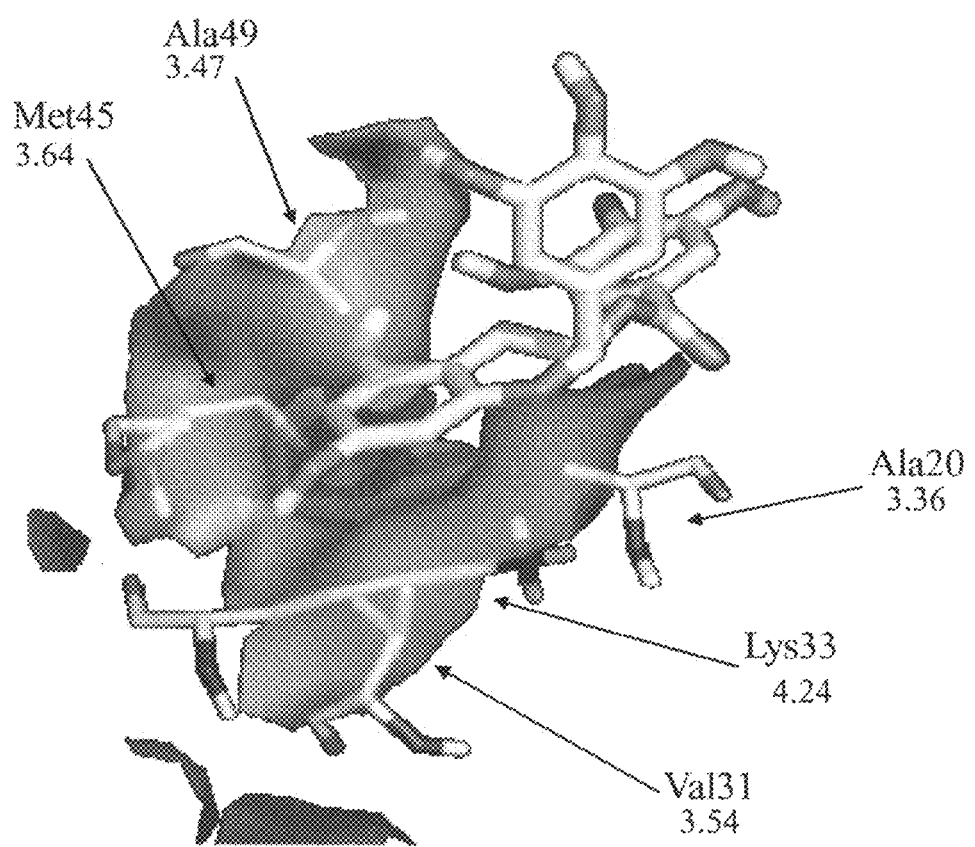
FIG. 2F shows the S1 hydrophobic pocket layered with a transparent surface and residues that interact hydrophobically along with distances from the residue to the A-C rings in (−)-EGCG.

The hydrophobic interactions between (−)-EGCG and the β5 subunit were analyzed. The chymotrypsin-like activity of the proteasome cleaves peptides after hydrophobic residues, such as the Tyr in the model fluorogenic substrate Suc-Leu-Leu-Val-Tyr-AMC. This Tyr would bind to the S1 hydrophobic pocket of the β5 subunit to allow for specific chymotrypsin-like cleavage of the AMC group. It seems that the A ring of (−)-EGCG mimics the Tyr residue of the proteasome peptide substrate: the hydrophobic portion of this aromatic ring is oriented in the middle of the S1 pocket between the side chains of Ala 49, Ala 20, and Lys 33 (with distances of 3.47, 3.36 and 4.24 Å, respectively; FIG. 2F). This conformation allows the hydrophilic hydroxyls of the A ring to project out of the two sides of the S1 hydrophobic pocket and participate in H bonding as described above. In addition, the side-walls of the S1 pocket that interact with (−)-EGCG are created by Met 45 and Val 31 (3.64 and 3.54 Å; FIG. 2F). Each of these hydrophobic or partially hydrophobic residues are less than 4.5 Å from (−)-EGCG (see FIG. 2F), suggesting that entropically driven hydrophobic interactions might indeed occur between the (−)-EGCG A-C rings and the S1 pocket. Therefore, inhibition kinetics, along with docking studies of (−)-EGCG bound to the proteasome β5 subunit, suggests a mechanistic model for how (−)-EGCG inhibits the proteasomal chymotrypsin-like activity.

Figure 4F:
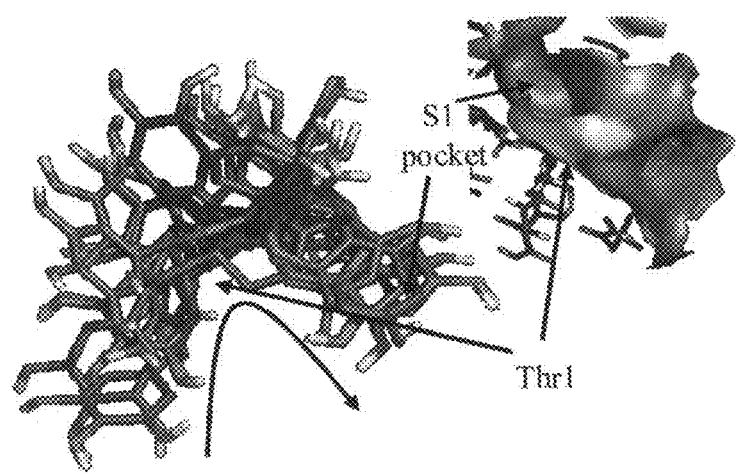
FIG. 4F shows an overlap of all the eight bound ligands and a bottom view of the saddle-shaped binding pocket. The surfaces are colored by atom type.

When (−)-EGCG binds the proteasome, a saddle shape is formed between the A-C rings extending past the ester bond and back down to the gallate moiety (FIG. 4E). The more flexible nature of the ester bond allows this conformation to occur so that (−)-EGCG might fit the saddle-shape formed by the bottom of the binding pocket (FIG. 4F, top/right). In fact, when the docked conformations of all the EGCG analogs are overlapped into one image, this saddle shape can be easily observed (FIG. 4F). This saddle-shaped conformation of EGCG possibly places additional strain on the scissile bond further lowering the activation energy for nucleophilic attack.

B. Docking of Other Natural and Synthetic EGCG Analogs

Whether this established model of (−)-EGCG inhibition could also be used to interpret the proteasome-inhibitory properties of other EGCG analogs was also investigated. Three natural, (−)-GCG, (−)-ECG and (−)-CG, and two synthetic, (+)-EGCG and (+)-GCG, polyphenols were chosen, all of which contain an ester bond (FIG. 1). Similar to (−)-EGCG, all of these five polyphenols potently inhibited the chymotrypsin-like activity of the rabbit 20S proteasome, with $IC_{50}$ values similar to those obtained using prokaryotic 20S proteasome (FIG. 3).

Each of these five polyphenols was docked to the 20S proteasome β5 subunit, using (−)-EGCG as a comparison (FIG. 3). The $B_5$ subunit is represented with a water accessible surface and colored by atom type (O-red, N-blue, C-gray, H-gray). For each compound, a single docking mode with the lowest free energy was selected after applying the two preset criteria. (+)-EGCG was found to be slightly more potent than (−)-EGCG with regard to purified 20S proteasome ($IC_{50}$ 170 nM vs. 205 nM; FIGS. 3A and 3B).

(+)-EGCG was oriented in the proteasome β5 subunit with a seemingly similar mode compared to (−)-EGCG, with the A-C rings in the S1 pocket, and the B ring in solvent, bridging the binding cleft (FIGS. 3B vs. 3A). The ester bond-carbon (and gallate group) were shifted only 0.38 Å away from Thr 1, as shown in FIG. 2D, but still resided over Thr 1 in a suitable position for a nucleophilic attack. [see FIG. 3B-1, for overlap of (+)-EGCG and (−)-EGCG]. The shift of this gallate group placed the carbonyl oxygen into the binding cavity created by Arg 19 and Thr 21 (also see FIG. 2E), allowing for an increased van der Waals interaction and a slightly more favorable binding free energy (−10.82 kcal/mol vs. −10.52 kcal/mol; FIGS. 3A and 3B), explaining the increased activity of this compound. A closer inspection revealed that (+)-EGCG had to flip over 180 degrees (in relation to the plane of the A-C rings) in order to attain a similar orientation/conformation. It is known that (−)-EGCG and (+)-EGCG have (2R,3R) and (2S,3S) stereochemistry, respectively (FIG. 1). This suggests that if the B ring and the gallate group of (+)-EGCG were to bind in the same position in three-dimensional space as (−)-EGCG, the A-C rings of (+)-EGCG would then have to rotate 180 degrees to compensate (FIG. 3B-1). Thus, the proteasome does not exhibit significant enantioselectivity for EGCG (FIG. 3) due to the partial symmetry of the A-C rings.

Figure 3C:
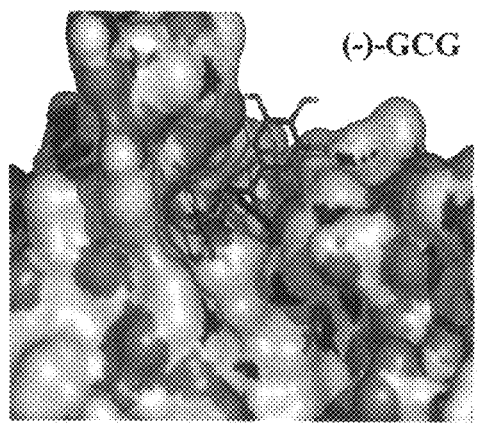
FIG. 3C shows the binding mode of (−)-GCG.
Figure 3D:
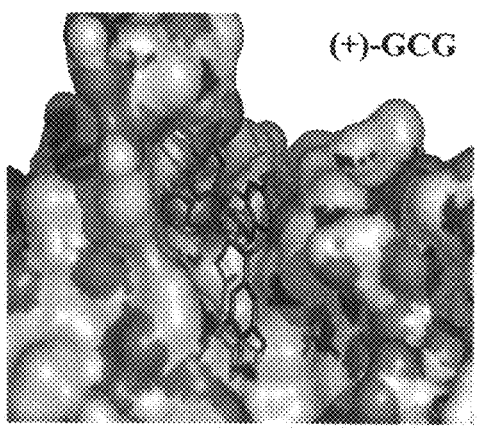
FIG. 3D shows the binding mode of (+)-GCG.
Figure 3E:
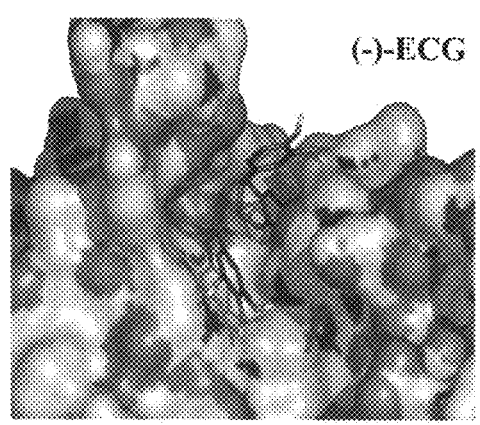
FIG. 3E shows the binding mode of (−)-ECG.

(−)-GCG is a non-"epi" compound that has trans stereochemistry about the C ring unlike (−)-EGCG which has cis stereochemistry (FIG. 1). The $IC_{50}$ value of (−)-GCG indicates that it is nearly 3 times less potent then (−)-EGCG (610 nM vs. 205 nM; FIGS. 3A and 3C), suggesting that the trans stereochemistry may not be as beneficial for binding to the proteasome's active site. In agreement with the experimental $IC_{50}$ values, the calculated binding free energy of (−)-GCG was −9.10 kcal/mol (FIG. 3C) compared with −10.52 kcal/mol for (−)-EGCG (FIG. 3A). For clarity, a two-dimensional scheme of the binding mode for (−)-GCG is also represented (FIG. 3G).

The synthetic (+)-GCG was more potent than the natural (−)-GCG (270 nM vs. 610 nM; FIGS. 3C and 3D). Consistent with their $IC_{50}$ values, a lower free energy is required for binding of (+)-GCG to β5 subunit than that of (−)-GCG (−10.33 kcal/mol vs. −9.10 kcal/mol; FIGS. 3C and 3D). (+)-GCG binds in a slightly different conformation compared with the rest of the other compounds (FIG. 3H). The unique (+)-trans stereochemistry of (+)-GCG allows for its B ring to form three H-bonds with Thr 21, Gly 23, and Tyr 170 (FIGS. 3D and 3H) instead of two as with (−)-EGCG (FIG. 2E). It also hydrophobically interacts with Tyr 170 (see FIG. 3H), which has stronger affinity than the binding cleft bridging conformation. The gallate group of (+)-GCG also extends further out of the pocket and forms three H-bonds with residues Val 129, Gly 130 and Ser 131 (FIGS. 3D and 3H), instead of two H-bonds as with (−)-EGCG (FIG. 2D). However, while this conformation may increase binding affinities at the B ring and gallate moieties, the A-C rings are pulled slightly out of the S1 pocket, reducing the total number of interactions that take place there. As a net result, a slight overall reduction in binding free energy and a slight reduction in in vitro proteasome-inhibitory activity occurs, as compared to (−)-EGCG (FIGS. 3D vs. 3A).

The natural GTP (−)-ECG lacks one hydroxyl group on its B ring (FIG. 1), which significantly reduces its solubility in water and also decreases its potency against 20S proteasome by more than three-fold, as compared to (−)-EGCG (710 nM vs. 205 nM; FIGS. 3A and 3E). (−)-ECG is also found to bind the β5 binding cleft with almost exactly the same binding mode as (−)-EGCG except for the loss of the H bond with the side chain of Thr 21 (FIGS. 3E vs. 2E). However, this did not increase the calculated binding free energy (−10.56 vs. −10.52 kcal/mol; FIG. 3E). Because the B ring is protruding into solvent and, as mentioned previously, the loss of this hydroxyl significantly decreases the solubility of (−)-ECG, Binding of this GTP to the proteasome might be affected in a manner that is not well accounted for by the solvation model used in the docking algorithms.

Figure 3F:
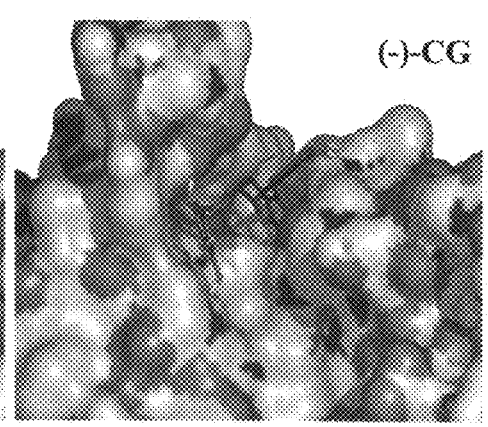
FIG. 3F shows the binding mode of (−)-CG.
Figures 3G, 3H:
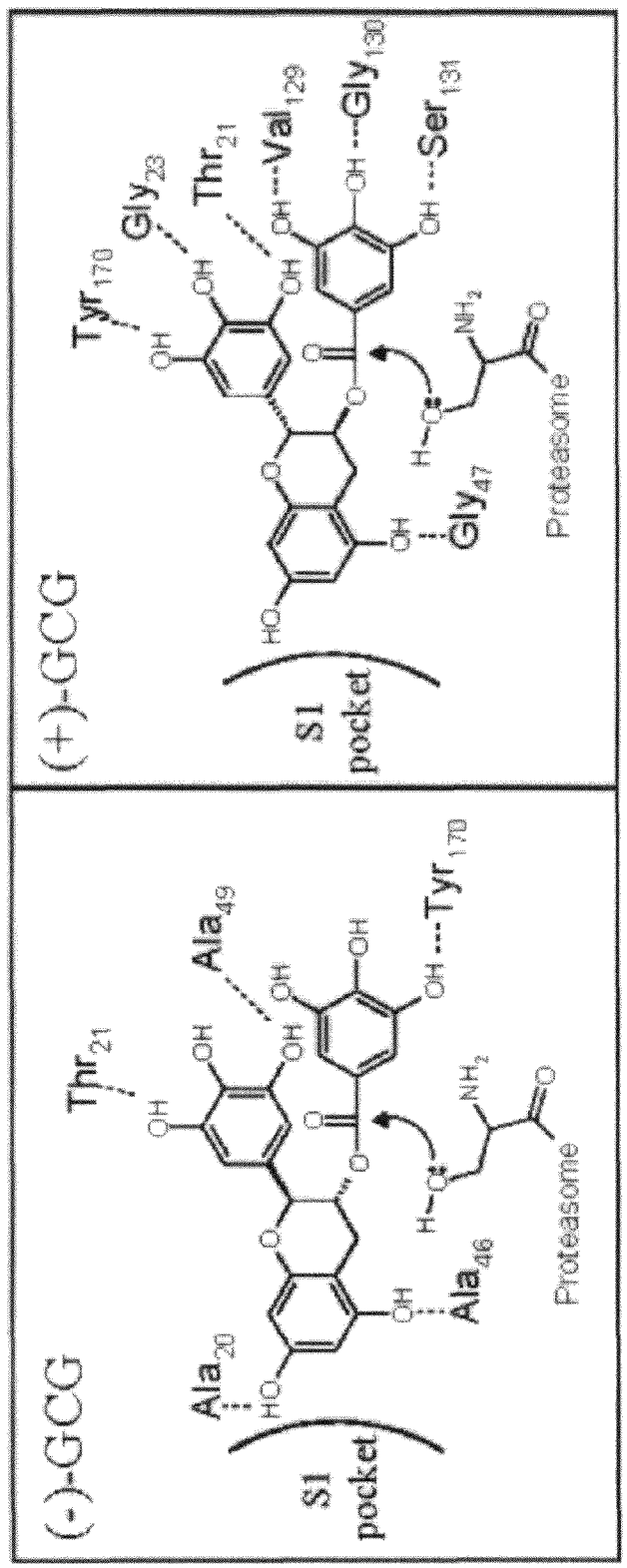
FIG. 3G shows a two-dimensional scheme for the binding mode of (−)-GCG. The dotted lines represent potential hydrogen bond formation and the S1 pocket designation represents hydrophobic interactions.
FIG. 3H shows a two-dimensional scheme for the binding mode of (+)-GCG.

The natural GTP (−)-CG is another non-epi compound with a trans stereochemistry (FIG. 1) and is less potent than (−)-EGCG (FIGS. 3F vs. 3A). Consistent with this, an increased ligand free energy is calculated for binding of (−)-CG to the proteasome's active site, thereby giving a net increase in binding free energy [−9.30 kcal/mol vs. −10.52 kcal/mol; and see the discussion about (−)-GCG].

Genistein, the predominant isoflavone found in soy products, was selected to test whether the developed computational model can be applied to a range of compounds with different chemical structures. Like (−)-EGCG, genistein also consists of a ring system similar to the A, C, and B rings of the GTPs (see FIG. 1), suggesting that genistein might be a proteasome inhibitor. But different from (−)-EGCG, genistein lacks the gallate group (see FIG. 1), which suggests that genistein would be less potent than (−)-EGCG.

Genistein was docked to yeast 20S proteasome. In 60 out of 100 runs with 5-million energy evaluations, genistein docks primarily in the S1 pocket of the active site of the proteasome β5 subunit. The B ring hydroxyl group of genistein lies in close proximity to Thr 1, and there are four potential hydrogen bonds that could be formed within the complex of genistein and the proteasomal β5 subunit. However, the binding free energy of genistein to β5 subunit was found to be −5.15 kcal/mol, much higher than that of (−)-EGCG (−10.52 kcal/mol; FIG. 3A). Consistent with its higher docking energy, genistein weakly inhibits the chymotrypsin-like activity of purified 20S proteasome with an $IC_{50}$ value of 26 μM (also see Table 1 and FIG. 5), in contrast to an $IC_{50}$ of 205 nM for (−)-EGCG (FIG. 3A). These data further demonstrates established computational model satisfactorily describes the EGCG-β5 interaction that is responsible for its proteasome-inhibitory activity.

Figure 5:
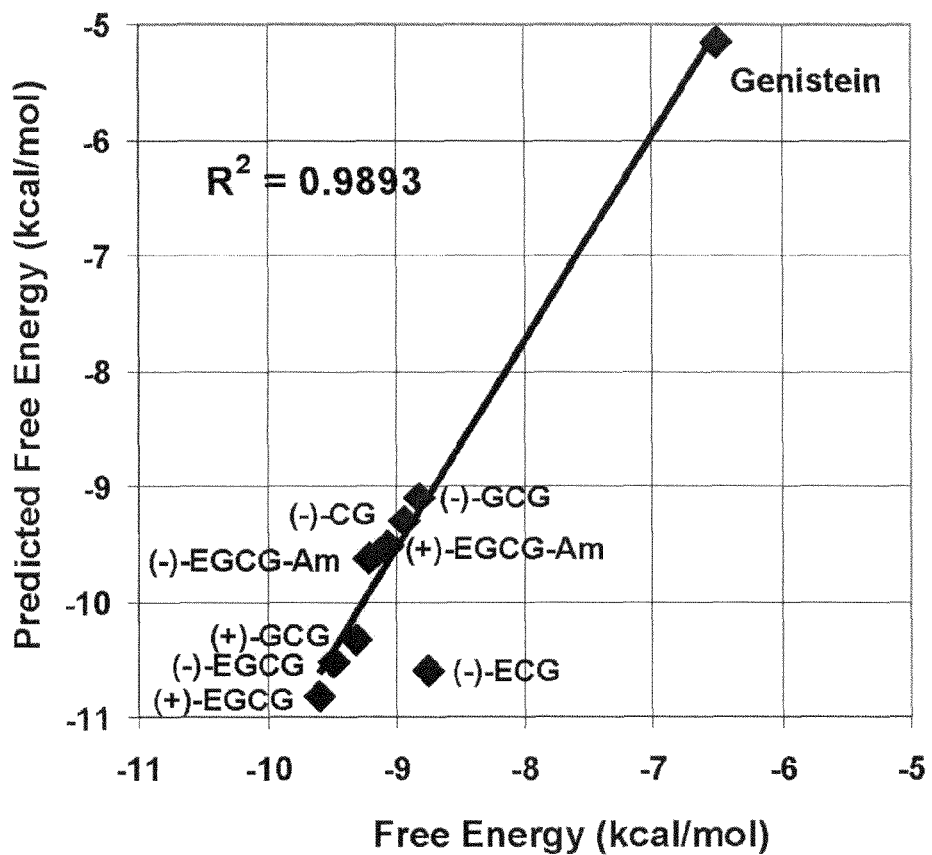
FIG. 5 shows a plot of predicted binding free energy (kcal/mol) against the actual proteasome-inhibitory activity (kcal/mol). A regression analysis yielded 0.9893 for the best fit $R^2$ value.

Finally, to compare the selected binding modes to the actual proteasome-inhibitory activities of each of the eight EGCG analogs and genistein, the predicted activity (binding-free energy) against the actual inhibitory activity ($IC_{50}$ values; converted to kcal/mol) (Table 1 and FIG. 5). A decrease in the docking free energy for 8 of the 9 compounds was correlated with an increase in the actual activity of each of these compounds. Only one compound, (−)-ECG, did not fit the linear relationship between the predicted and actual activity (FIG. 5). This significant loss in actual activity of (−)-ECG, which is not in congruence with the calculated binding free energy, may be due to the orientation and solvation issues mentioned previously. A regression analysis $R^2$ value of 0.9893 was determined for a best-fit line, not including the values generated for (−)-ECG.

TABLE 1

Predicted vs. Observed Binding Free Energies

| Compound | Predicted ΔG° (kcal/mol) | $IC_{50}$ | $-RTln(1/IC_{50})^a$ |
|---|---|---|---|
| (+)-EGCG | −10.82 | 170 nM | −9.60 |
| (−)-EGCG | −10.52 | 205 nM | −9.49 |
| (+)-GCG | −10.33 | 270 nM | −9.32 |
| (−)-ECG | −10.56 | 710 nM | −8.72 |
| (−)-EGCG-Amide | −9.63 | 320 nM | −9.21 |
| (+)-EGCG-Amide | −9.52 | 405 nM | −9.07 |
| (−)-CG | −9.30 | 505 nM | −8.93 |
| (−)-GCG | −9.10 | 610 nM | −8.81 |
| genistein | −5.15 | 26 μM | −6.50 |

$^a$Note that $IC_{50}$ is proportional to $K_i$. Since $K_i$ is the equilibrium constant for the dissociation of the enzyme-inhibitor complex, and the binding free energy (ΔG°) is related to the equilibrium constant for the association of enzyme with inhibitor, ΔG° is proportional to $-RTln(1/IC_{50})$, which is identical to $+RTln(IC_{50})$.

Example 11

(−)-EGCG Proteasome Inhibition

To investigate the nature of (−)-EGCG-mediated proteasome inhibition, a dialysis experiment was performed. A purified prokaryotic 20S proteasome was pre-incubated for one hour at 37° C. with either 10 μM (−)-EGCG or its control solvent ($H_2O$), followed by overnight co-incubation at 4° C. with or without dialysis.

Figure 6:
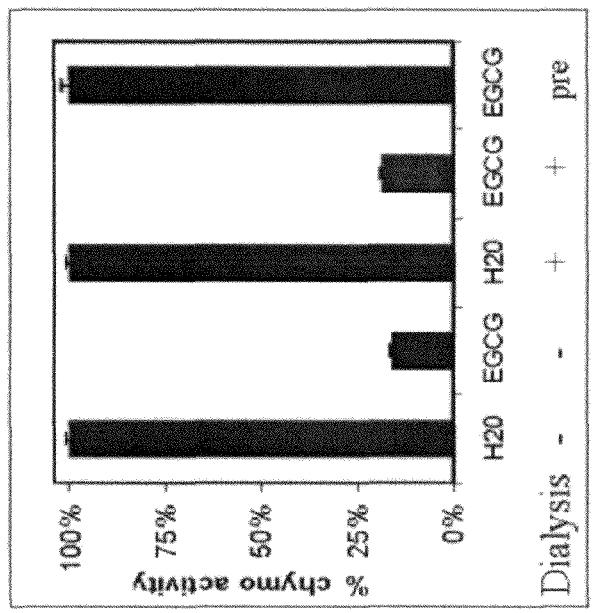
FIG. 6 shows a bar graph comparing the percentage of chymotrypsin activity when a proteasomal cell comes into contact with any of the agents listed. A minus sign indicates that no dialysis took place; a plus signs indicates that dialysis took place.

FIG. 6 shows that, in the absence of dialysis, (−)-EGCG was able to inhibit the chymotrypsin-like activity of the prokaryotic 20S proteasome by 85%. More importantly, overnight dialysis of the EGCG-proteasome mixture did not change the outcome: 1 h pre-incubation of (−)-EGCG still caused 81% inhibition of the proteasomal chymotrypsin-like activity.

As a control, when an aliquot of (−)-EGCG was first dialyzed overnight and then added to the purified 20S proteasome, no inhibition was observed (FIG. 6, EGCG pre). This result demonstrates that (−)-EGCG is either an irreversible or a tight-binding inhibitor of the chymotrypsin-like activity of the proteasome.

In the second experiment (−)-EGCG at 1 μM was pre-incubated with (SDS-pre) or without 0.01% SDS (no SDS) for 1 hour, followed by addition of eukaryotic 20S proteasome (0.02 μg) and suc-LLVY-AMC (20 μM). "SDS-post" represents the same treatment as "no SDS" except 0.01% SDS was added 1 hour after addition of the proteasome, (−)-EGCG and the substrate. AMC liberation was measured by fluorescence at each indicated time point and the percentage of chymotrypsin activity was determined. Values are means from 4 independent experiments, and error bars represent standard deviations.

Figure 22A:
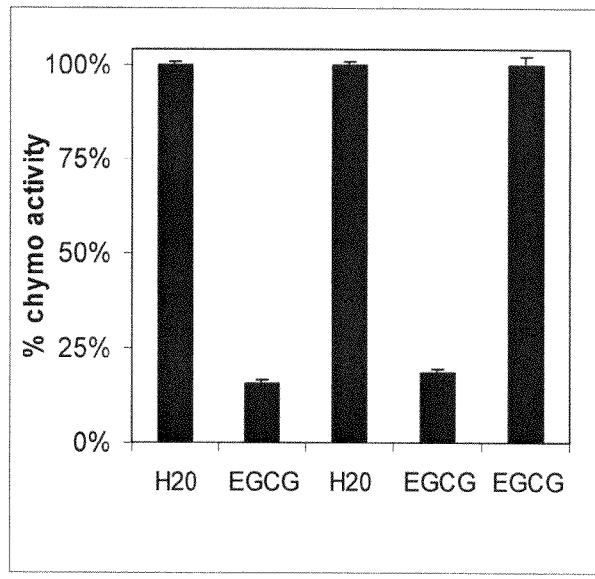
FIG. 22A shows a bar graph demonstrating the effect of dialysis on proteasome inhibition.
Figure 22B:
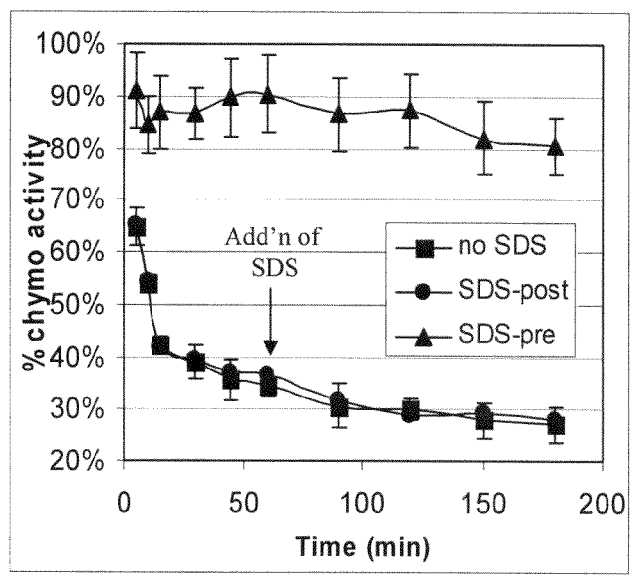
FIG. 22B SDS-post-treatment does not inhibit (−)-EGCG-mediated proteasome inhibition.

In the second experiment, (−)-EGCG at 1 μM potently inhibited the chymotrypsin-like activity of a purified eukaryotic (rabbit) 20S proteasome (up to 75%; FIG. 22B, no SDS). However, pre-incubation with 0.01% SDS for 1 hour resulted in a significant loss of the potency of (−)-EGCG (to 10-20% of inhibition; FIG. 22B, SDS-pre), suggesting that SDS antagonizes EGCG's ability to inhibit the proteasome. When (−)-EGCG was pre-incubated with the 20S proteasome for 1 hour, addition of SDS could not reverse the EGCG-mediated proteasome inhibition (FIG. 22B, SDS-post), demonstrating that EGCG had already inhibited the proteasome after 1 hour and this inhibition could not be antagonized by SDS. In the absence of (−)-EGCG, 0.01% SDS was able to increase the 20S proteasomal activity.

The result of the second experiment demonstrates that the mode of (−)-EGCG action is an irreversible inhibition by a covalent bond formation, not tight binding inhibition. Furthermore, the time-dependent inhibition of the proteasomal chymotrypsin-like activity by (−)-EGCG: 35% at 5 min, 62% at 30 min, and 70-80% after 1 to 3 hours (FIG. 22B, no SDS) is characteristic for a mechanism-based inhibitor.

Kinetic analysis and X-ray diffraction studies using the specific proteasome inhibitor lactacystin have demonstrated that the ester bond of the inhibitor covalently modifies the N-terminal threonine of the β5 subunit, which is critical for proteasome inhibition. Since (−)-EGCG contains an ester bond (FIG. 15) and inhibits the proteasome irreversibly in a time-dependent manner (FIGS. 22A and 22B), it is probable that a lactacystin-like reaction could occur with (−)-EGCG.

The prokaryotic proteasome was used because it demonstrated more stable kinetics after overnight dialysis, although a similar result can be obtained using eukaryotic proteasome.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of a) increasing the relative proportion of cells occupying the $G_1$ phase of the mitotic cell cycle within prostate tumor or cancer cells and leukemia cells; or b) inducing apoptosis in prostate tumor or cancer cells and leukemia cells; said method comprising contacting the prostate tumor or cancer cells and leukemia cells with an effective amount of a compound having a formula of:

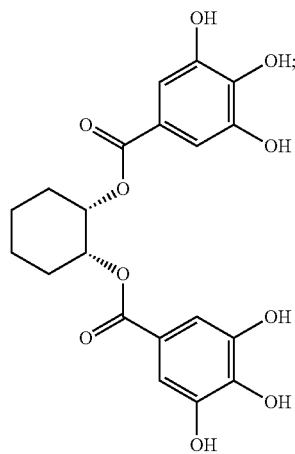

GTP-1

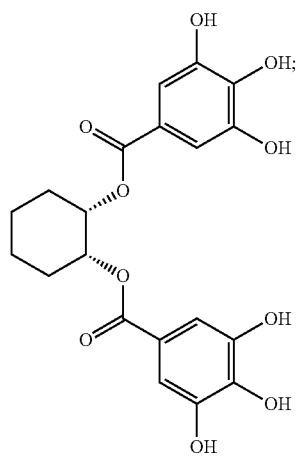

GTP-2

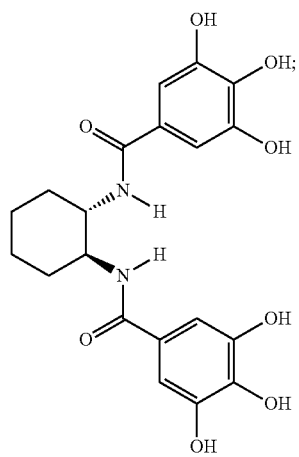

GTP-3

-continued

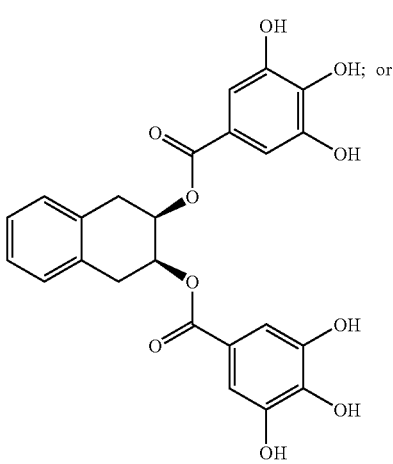

GTP-4

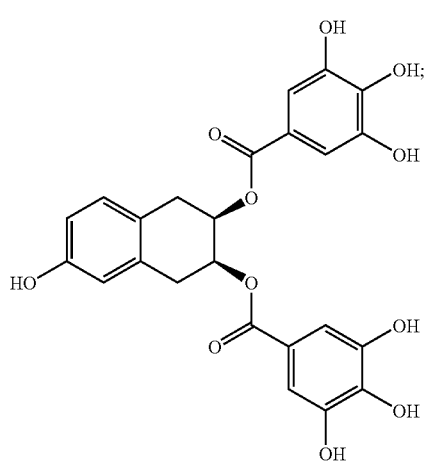

GTP-5 or a pharmaceutically acceptable salt of said compound; or a composition comprising said compound, or a pharmaceutically acceptable salt of said compound.

2. The method according to claim 1, wherein said cells are human cells.

3. The method according to claim 1, wherein said contacting occurs in vivo, and said contacting comprises administering the compound to a patient by a route selected from the group consisting of orally, parenterally, subcutaneously, intravenously, intramuscularly, intraperitoneally, intraarterially, transdermally, and via a mucus membrane.

4. The method according to claim 1, wherein said contacting occurs in vitro.

5. The method according to claim 1, wherein said compound has less than 100% optical purity.

6. The method according to claim 1, wherein said compound is optically pure.

7. The method according to claim 1, wherein said composition comprises a pharmaceutically acceptable carrier or diluent.

8. The method according to claim 1, wherein said compound has the formula of:

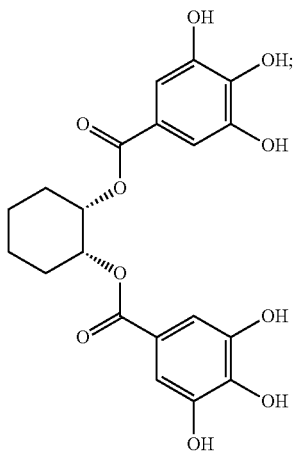

GTP-1 or a pharmaceutically acceptable salt of said compound; or a composition comprising said compound, or a pharmaceutically acceptable salt of said compound.

9. The method according to claim 1, wherein said compound has the formula of:

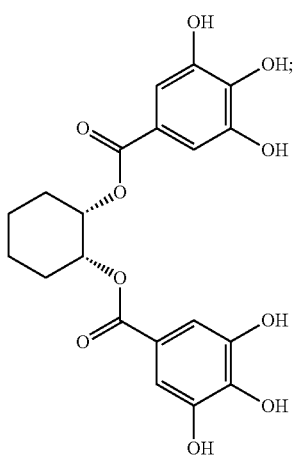

GTP-2 or a pharmaceutically acceptable salt of said compound; or a composition comprising said compound, or a pharmaceutically acceptable salt of said compound.

10. The method according to claim 1, wherein said compound has the formula of:

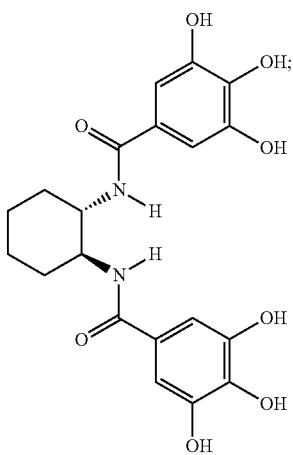

GTP-3 or a pharmaceutically acceptable salt of said compound; or a composition comprising said compound, or a pharmaceutically acceptable salt of said compound.

11. The method according to claim 1, wherein said compound has the formula of:

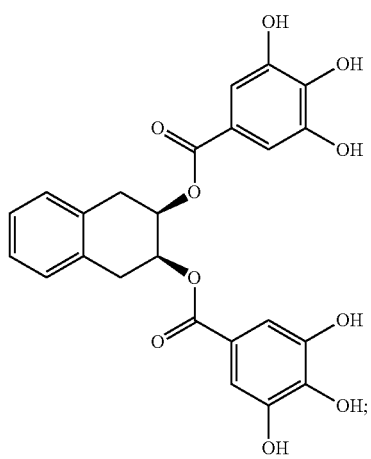

GTP-4 or a pharmaceutically acceptable salt of said compound; or a composition comprising said compound, or a pharmaceutically acceptable salt of said compound.

12. The method according to claim 1, wherein said compound has the formula of:

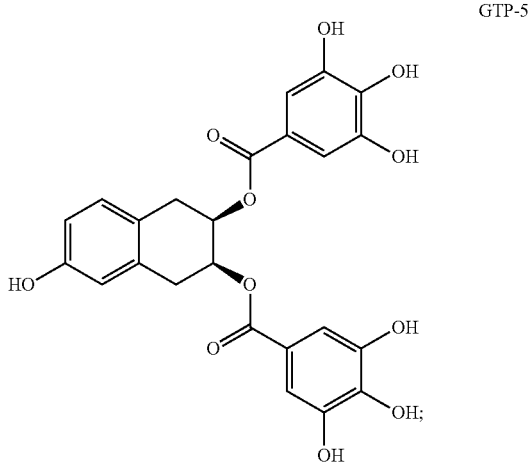

GTP-5 or a pharmaceutically acceptable salt of said compound; or a composition comprising said compound, or a pharmaceutically acceptable salt of said compound.

13. The method according to claim 1, wherein said cells are prostate tumor or cancer cells.

14. The method according to claim 1, wherein said cells are leukemia cells.

\* \* \* \* \*

UNITED STATES PATENT AND TRADEMARK OFFICE
CERTIFICATE OF CORRECTION

PATENT NO. : 8,058,310 B2
APPLICATION NO. : 12/660351
DATED : November 15, 2011
INVENTOR(S) : Q. Ping Dou, Tak-Hang Chan and David M. Smith It is certified that error appears in the above-identified patent and that said Letters Patent is hereby corrected as shown below:

Column 1,
Line 61, "unmodified p27' that" should read --unmodified p27 that--.

Column 2,
Line 8, "*Biomarkers Prey*" should read --*Biomarkers Prev*--.

Column 6,
Line 35, "cylcoalkenyl" should read --cycloalkenyl--.

Column 7,
Line 11, "heterocylcoalkyl" should read --heterocycloalkyl--.

Column 10,
Line 56, "invention. the following" should read --invention, the following--.

Column 15,
Lines 25-26, "for 30 mM at" should read --for 30 min at--.
Lines 37-38, "with 10(-)-EGCG" should read --with 10 µM (-)-EGCG--.

Column 17,
Line 64, "IκB-a" should read --IκB-α--.

Column 19,
Line 67, "of -4,400" should read --of ~1,400--.

Column 21,
Line 65, "NMR" should read --$^1$H NMR--.

Signed and Sealed this
Seventeenth Day of April, 2012

David J. Kappos
*Director of the United States Patent and Trademark Office*

CERTIFICATE OF CORRECTION (continued)
U.S. Pat. No. 8,058,310 B2

Column 23,
Line 51, "98.4 mmol" should read --98.4 µmol--.

Column 24,
Line 12, "cis-(±)—N-[5,7" should read --*cis*-(±)-N-[5,7--.

Column 26,
Line 58, "P27" should read --p27--.

Column 33,
Line 36, "Binding" should read --binding--.

Column 36,
Line 25, GTP-2 structure,

" " should read -- 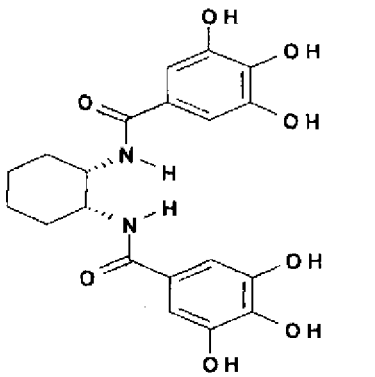 --.

Column 38,
Line 45, GTP-2 structure,

" " should read -- 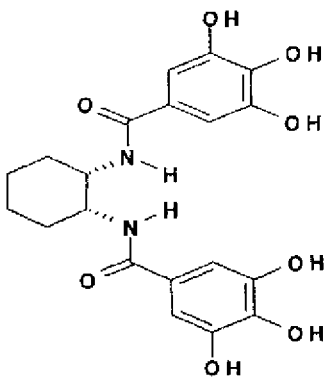 --.